(12) United States Patent
Osawa et al.

(10) Patent No.: US 12,070,207 B2
(45) Date of Patent: Aug. 27, 2024

(54) SUTURING DEVICE

(71) Applicant: BROTHER KOGYO KABUSHIKI KAISHA, Nagoya (JP)

(72) Inventors: Naokatsu Osawa, Nagoya (JP); Ryuta Iijima, Nagoya (JP); Masashi Ichihashi, Mizuho (JP); Kohei Terada, Kiyosu (JP)

(73) Assignee: BROTHER KOGYO KABUSHIKI KAISHA, Nagoya (JP)

( * ) Notice: Subject to any disclaimer, the term of this patent is extended or adjusted under 35 U.S.C. 154(b) by 709 days.

(21) Appl. No.: 17/085,802

(22) Filed: Oct. 30, 2020

(65) Prior Publication Data

US 2021/0045733 A1 Feb. 18, 2021

Related U.S. Application Data

(63) Continuation of application No. PCT/JP2019/012032, filed on Mar. 22, 2019.

(30) Foreign Application Priority Data

May 1, 2018 (JP) .................................. 2018-088471

(51) Int. Cl.
*A61B 17/04* (2006.01)
*A61B 17/06* (2006.01)
(52) U.S. Cl.
CPC ...... *A61B 17/0482* (2013.01); *A61B 17/0485* (2013.01); *A61B 17/06061* (2013.01)
(58) Field of Classification Search
CPC .......... A61B 17/0482; A61B 17/06061; A61B 2017/0472; A61B 2017/0474;
(Continued)

(56) References Cited

U.S. PATENT DOCUMENTS

| 4,600,007 A | 7/1986 | Lahodny et al. |
| 4,644,953 A * | 2/1987 | Lahodny ................ A61B 17/42 |
| | | 606/174 |

(Continued)

FOREIGN PATENT DOCUMENTS

| CN | 102164548 A | 8/2011 |
| CN | 202397539 U | 8/2012 |

(Continued)

OTHER PUBLICATIONS

Oct. 12, 2021 Office Action issued in Japanese Patent Application No. 2018-088471.

(Continued)

*Primary Examiner* — Elizabeth Houston
*Assistant Examiner* — Lauren Dubose
(74) *Attorney, Agent, or Firm* — Oliff PLC

(57) ABSTRACT

A suturing device includes first and second holding members, a plurality of needles, a needle moving mechanism, and a suture hook. The first and second holding members are configured to move toward and away from each other to sandwich therebetween edges of a cut. The needles are disposed at the first holding member and aligned in a needle arrangement direction with their points pointing to the second holding member. The needles are configured to hold a suture at tips thereof. The needle moving mechanism is configured to move the plurality of needles toward the second holding member. The suture hook is disposed at the second holding member and configured to move along the needle arrangement direction to catch the suture that has reached the second holding member via the edges of the cut by movement of the needles toward the second holding member by the needle moving mechanism.

19 Claims, 24 Drawing Sheets

(58) Field of Classification Search
CPC ............ A61B 17/0487; A61B 17/0625; A61B 17/0485; A61B 2017/06042; A61B 17/0469; A61B 17/0491; A61B 2017/0496; A61B 2017/00557; B65H 69/04; B65H 69/043; B65B 13/26; D04B 3/02; D04B 31/00; D04B 33/00
USPC .......................................................... 289/1.2
See application file for complete search history.

(56) References Cited

U.S. PATENT DOCUMENTS

| | | | | |
|---|---|---|---|---|
| 5,728,112 | A * | 3/1998 | Yoon | A61B 17/04 |
| | | | | 606/139 |
| 6,117,144 | A * | 9/2000 | Nobles | A61B 17/0057 |
| | | | | 606/147 |
| 2003/0065336 | A1 | 4/2003 | Xiao | |
| 2010/0113873 | A1 | 5/2010 | Suzuki et al. | |
| 2011/0178536 | A1 | 7/2011 | Kostrzewski | |
| 2011/0301620 | A1 | 12/2011 | Di Betta et al. | |
| 2012/0035623 | A1* | 2/2012 | Bagaoisan | A61B 17/0482 |
| | | | | 606/144 |
| 2012/0037686 | A1 | 2/2012 | Hessler | |
| 2012/0160721 | A1 | 6/2012 | Shelton, IV et al. | |
| 2013/0178877 | A1 | 7/2013 | Bender et al. | |

FOREIGN PATENT DOCUMENTS

| | | |
|---|---|---|
| JP | S60-085736 A | 5/1985 |
| JP | 2011-147770 A | 8/2011 |
| JP | 2012-035075 A | 2/2012 |
| JP | 2014-518682 A | 8/2014 |
| KR | 10-2015-0054345 A | 5/2015 |

OTHER PUBLICATIONS

Dec. 9, 2021 Extended European Search Report issued in European Patent Application No. 19796242.6.
Jun. 18, 2019 International Search Report issued in International Patent Application No. PCT/JP2019/012032.
Nov. 3, 2020 International Preliminary Report on Patentability issued in International Patent Application No. PCT/JP2019/012032.
Sep. 28, 2023 Office Action issued in Chinese Patent Application No. 201980028788.8.

* cited by examiner

SUTURING DEVICE

CROSS-REFERENCE TO RELATED APPLICATION

This is a continuation application of International Application No. PCT/JP2019/012032 filed on Mar. 22, 2019 which claims priority from Japanese Patent Application No. 2018-088471 filed on May 1, 2018. The entire contents of the earlier applications are incorporated herein by reference.

TECHNICAL FIELD

Aspects disclosed herein relate to a suturing device that stitches a relatively wide area in edges of a cut at once using a suture without using metal staples.

BACKGROUND

A known suturing device is used for closing edges of a cut with staples in surgical operations. Such a suturing device sutures a relatively wide area in edges of a cut (e.g., edges of a cut entirely) at once.

SUMMARY

The staples used for suturing may be made of metal, and in some cases, permanently remain inside a patient's body. In such a case, nevertheless, one or more of the staples may come off in the patient's body and this may cause pain to the patient. In staple suturing, a fastening strength to secure a closure might not be adjustable depending on types or conditions of portions to be sutured. In addition, staple suturing may be unsuitable for a relatively soft portion to be sutured.

On the other hand, suturing using forceps with a needle and a suture threaded through the needle may have flexibility in adjustment. For example, a range to be sutured may be adjustable by changing the number of stitches to be placed and a fastening strength to secure a closure may be adjustable depending on types or conditions of portions to be sutured. In such suturing, nevertheless, stitches may be placed, one by one, to close a cut. Such suturing may be a skilled technique, and in a case where a cut to be sutured is wide, it may take a relatively long time for suturing edges of a cut.

Accordingly, aspects of the disclosure provide a suturing device that may enable a user with less experience to stitch edges of a wide cut with a suture for a relatively short time.

In one or more aspects of the disclosure, a suturing device may include first and second holding members, a plurality of needles, a needle moving mechanism, and a suture hook. The first and second holding members may be configured to move toward and away from each other to sandwich therebetween edges of a cut. The plurality of needles may be disposed at the first holding member and aligned in a needle arrangement direction with their points pointing to the second holding member. The plurality of needles may be configured to hold a suture at tips thereof and penetrate the edges of the cut. The needle moving mechanism may be configured to move the plurality of needles toward the second holding member, thereby allowing the plurality of needles holding the suture at the respective tips to penetrate the edges of the cut. The suture hook may be disposed at the second holding member and configured to move along the needle arrangement direction to catch the suture that has reached the second holding member via the edges of the cut by movement of the plurality of needles toward the second holding member by the needle moving mechanism.

DETAILED DESCRIPTION

Illustrative embodiments of the disclosure will be described with reference to the accompanying drawings.

First Illustrative Embodiment

Figure 1:
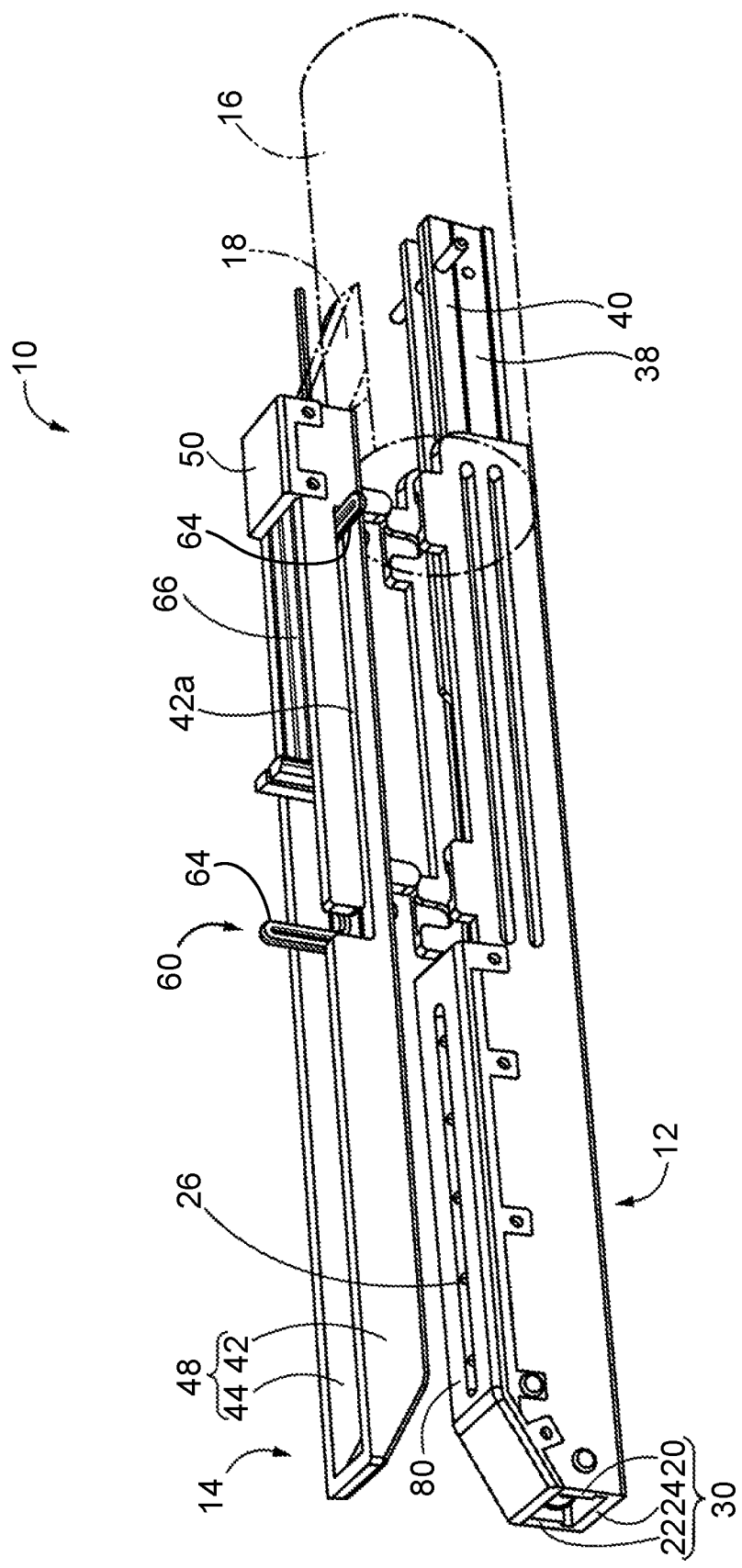
FIG. 1 is a perspective view of a suturing device according a first illustrative embodiment of the disclosure.
Figure 2:
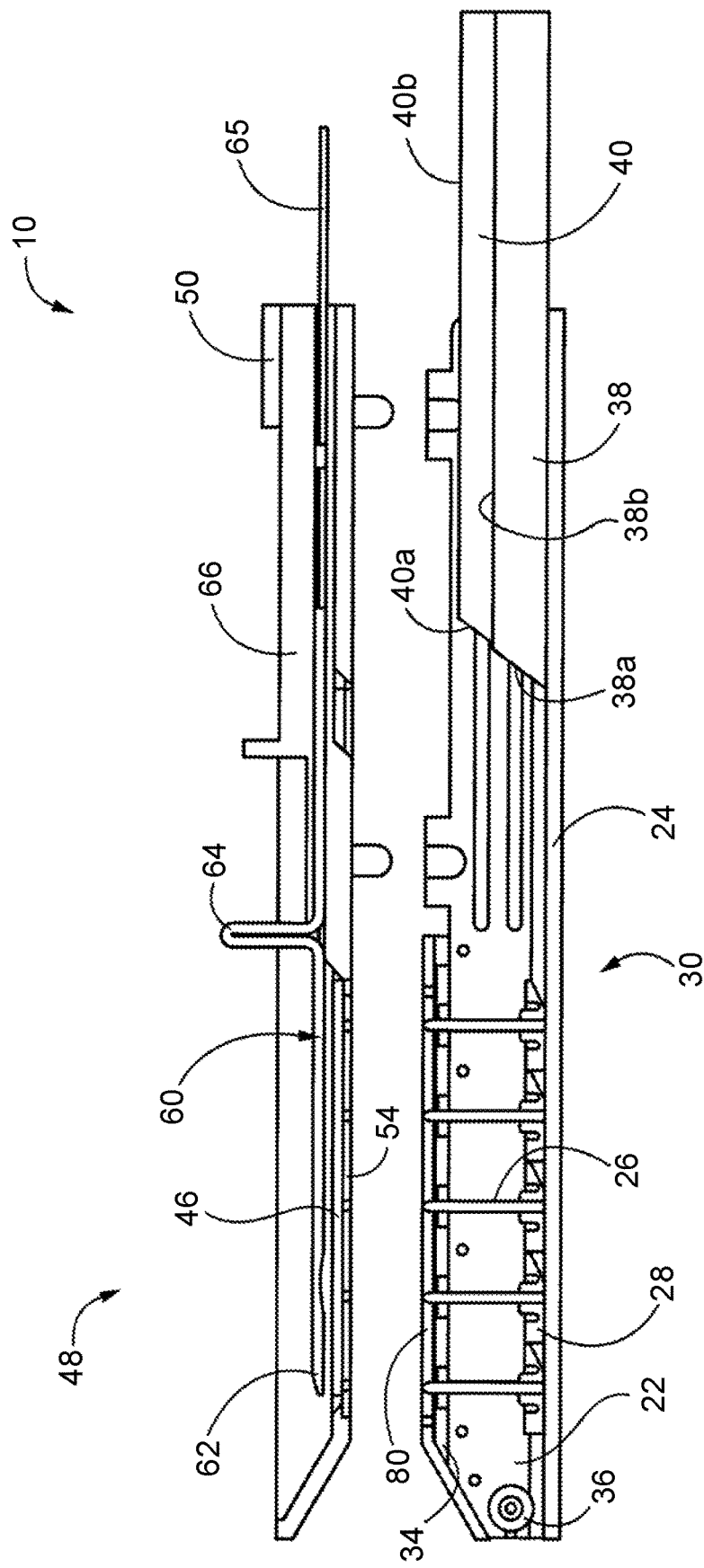
FIG. 2 is a sectional view illustrating respective configurations of a first casing and a second casing for holding therebetween edges of a cut in the suturing device according the first illustrative embodiment of the disclosure.

As illustrated in FIGS. 1 and 2, a suturing device 10 includes a couple of casings including a first casing 12 and a second casing 14 at its distal end portion. The first casing 12 and the second casing 14 each have an elongated box shape. A known open/close mechanism is equipped with the first casing 12 and the second casing 14. The open/close mechanism is configured to open and close the suturing device 10 to move the first casing 12 and the second casing 14 relatively away from and toward each other. As illustrated in FIG. 1, the open/close mechanism is disposed at a distal end of a tubular member 16 having an outside diameter of approximately 5 to 10 mm. For example, the tubular member 16 is inserted into an abdominal cavity of a living body during surgery. The open/close mechanism includes a jaw mount, a cylindrical drive shaft, and a cam block. While fixedly supporting the first casing 12, the jaw mount supports the second casing 14 to be movable toward or away from the first casing 12. The drive shaft has a diameter slightly smaller than the tubular member 16. The drive shaft is slidably engaged in the tubular member 16 and is movable along a longitudinal axis of the tubular member 16. The cam block is disposed at a distal end of the drive shaft. The second casing 14 includes a cam arm 18 at its proximal end. In response to the drive shaft being operated to move toward the second casing 14, the cam arm 18 is pressed against the cam block, and thus, the second casing 14 moves toward the first casing 12. In response to the drive shaft being operated to move away from the second casing 14, the cam arm 18 is separated from the cam block, and thus, the second casing 14 moves away from the first casing 12 by an urging force of a return spring disposed in the jaw mount. The first casing 12 and the second casing 14 may function as a first holding member and a second holding member, respectively, that may hold therebetween edges of a cut T, for example, a tissue of a living body. In other embodiments, for example, the first casing 12 and the second casing 14 may be coupled to each other at their proximal ends by a certain pin, thereby being pivotable about the pin to be relatively moved away from and toward each other.

Figure 5:
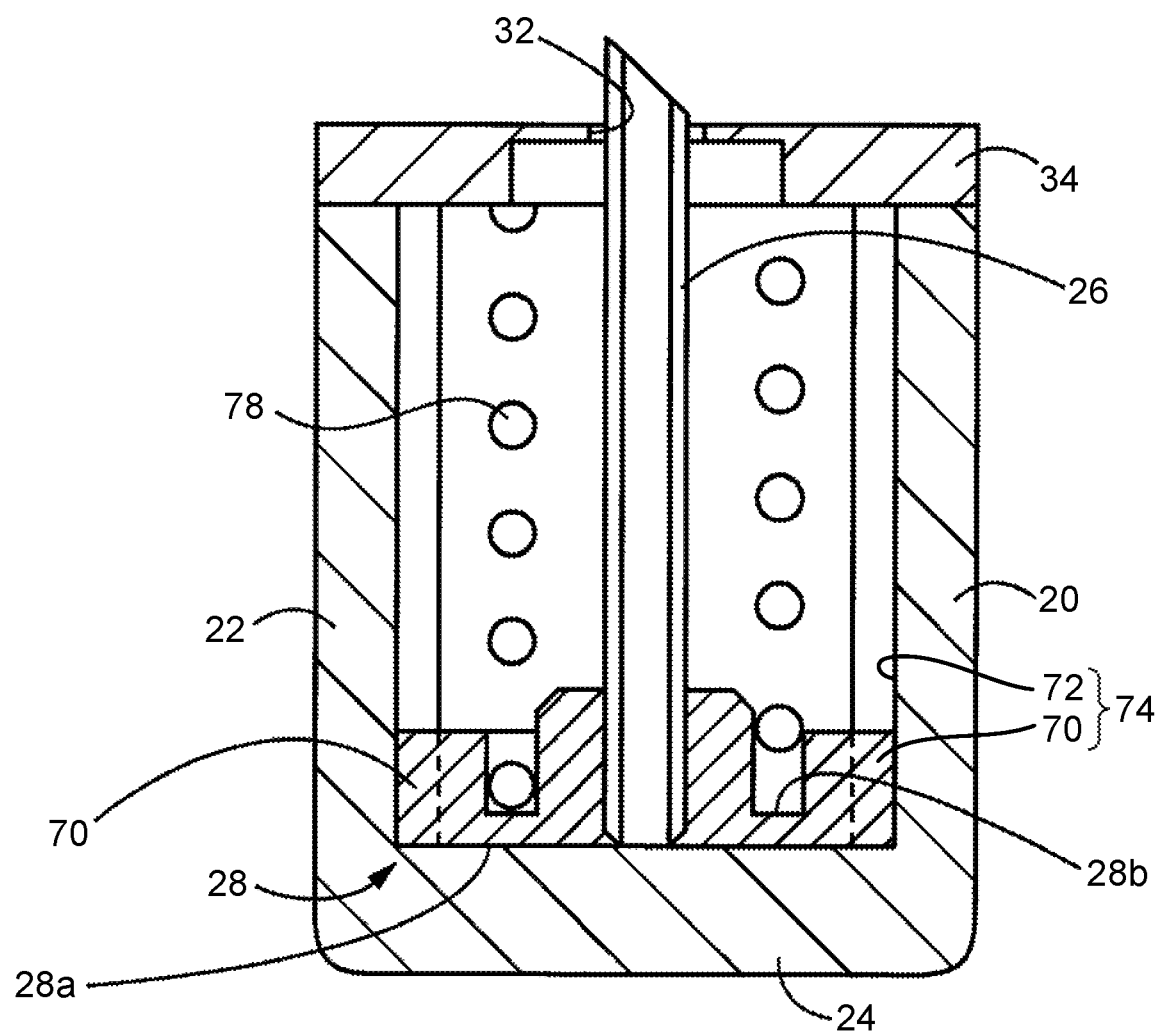
FIG. 5 is a cross-sectional view taken along line V-V of FIG. 4 according the first illustrative embodiment of the disclosure.

As illustrated in FIGS. 1 and 2, the first casing 12 includes a pair of side walls 20 and 22 and a bottom wall 24 that are integral with each other. The side walls 20 and 22 are elongated walls extending parallel to each other. Each of the side walls 20 and 22 has one end and the other end opposite to each other. The one ends of the respective side walls 20 and 22 face the second casing 14 and are closer to the second casing 14 than the other ends of the respective side walls 20 and 22 are to the second casing 14. The bottom wall 24 is an elongated wall and connects between the other ends of the side walls 20 and 22. The first casing 12 accommodates needle stands 28 in its distal end portion in a longitudinal axis thereof. Each needle stand 28 holds a needle 26. In the first illustrative embodiment, for example, five needles 26 are provided. As illustrated in FIGS. 1, 2 and 5, for example, the first casing 12 includes a first casing body 30, a plurality of holes 32 (only one of which is illustrated in FIG. 5), and a pressing plate 34. As illustrated in FIG. 5, the first casing body 30 has a U-shape in cross section and an open end facing the second casing 14. The pressing plate 34 has the holes 32 penetrating therethrough to allow a corresponding needle 26 to pass through the pressing plate 34. The pressing plate 34 is disposed to close a distal end portion of the open end of the first casing body 30. As illustrated in FIG. 2, the first casing 12 further includes a first needle pusher 38 and a second needle pusher 40. When the suturing device 10 is oriented as illustrated in FIG. 2, the first needle pusher 38 and the second needle pusher 40 are accommodated in a proximal end portion of the first casing body 30 in the longitudinal axis of the first casing 12. The first needle pusher 38 and the second needle pusher 40 are configured to move the needles 26 up and down. The first needle pusher 38 is disposed above the bottom wall 24 and the second needle pusher 40 is disposed above the first needle pusher 38 in the first casing body 30. In such a state, the first needle pusher 38 and the second needle pusher 40 are slidable along the longitudinal axis of the first casing 12. The first needle pusher 38 and the second needle pusher 40 are an example of a pusher. The first needle pusher 38 and the second needle pusher 40 are connected to respective operating rods disposed in the tubular member 16. Each of the first needle pusher 38 and the second needle pusher 40 is configured to move between a distal-end side position and a proximal-end side position in the first casing body 30 by operation of a corresponding operating rod.

Figure 8:
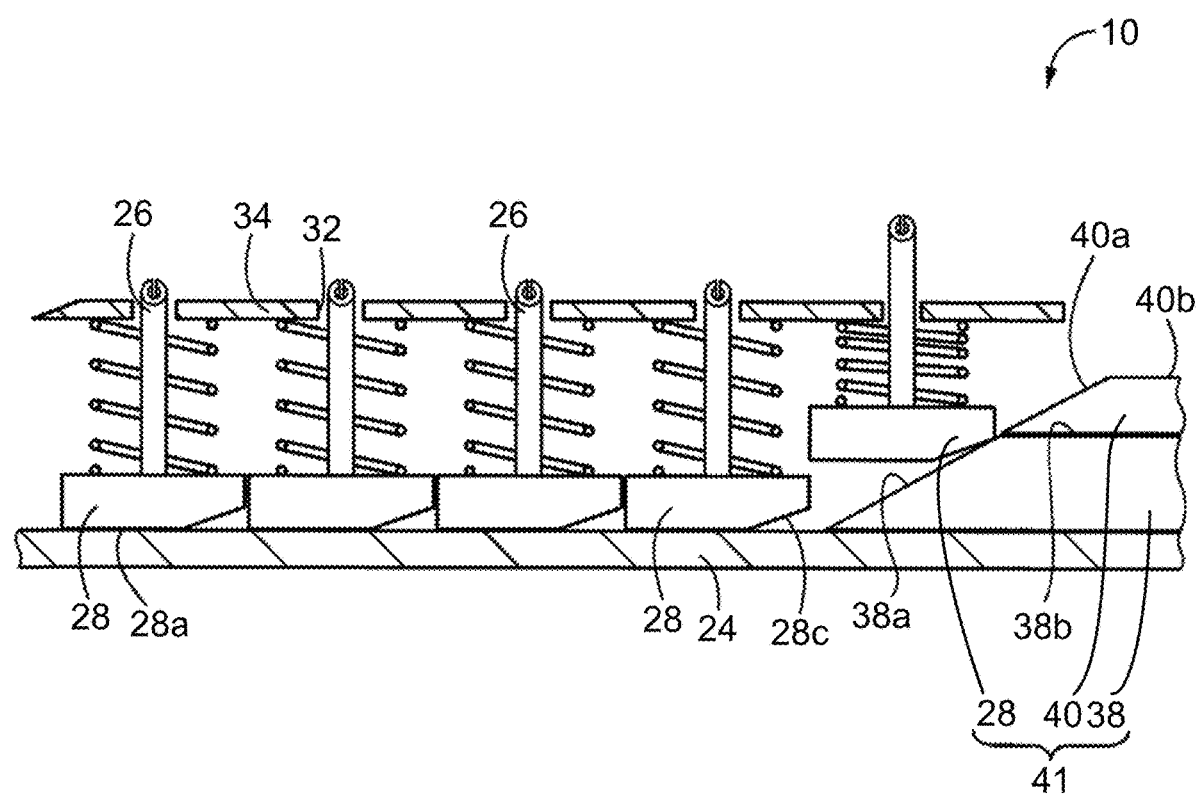
FIG. 8 is a side view of a main portion of the first casing of FIGS. 1 and 2 for explaining up and down movement of the needle stands disposed inside the first casing according the first illustrative embodiment of the disclosure.

The first needle pusher 38 and the second needle pusher 40 may be elongated members each having a rectangular shape in cross section. The first needle pusher 38 and the second needle pusher 40 each have a width slightly narrower than a gap between the side walls 20 and 22 of the first casing body 30. The first needle pusher 38 and the second needle pusher 40 are guided independently of each other by the side walls 20 and 22 along the longitudinal axis of the first casing 12 when being operated by the respective operating rods. As illustrated in FIG. 8, the first needle pusher 38 includes a first inclined surface 38a and a first positioning surface 38b. The first needle pusher 38 has the first inclined surface 38a at its leading end. The first inclined surface 38a is configured to engage bottom surfaces 28a of the needle stands 28 one after another to push up the needle stands 28 from the bottom wall 24 (e.g., move the needle stands 28 toward the second casing 14). The first positioning surface 38b may be a flat surface contiguous from the first inclined surface 38a, and is configured to position the respective needle stands 28 at a first height. The first height is constant and predetermined. The second needle pusher 40 is disposed on the first needle pusher 38. The second needle pusher 40 includes a second inclined surface 40a and a second positioning surface 40b. The second needle pusher 40 has the second inclined surface 40a at its leading end. The second inclined surface 40a is configured to engage the bottom surfaces 28a of the needle stands 28 that have been raised by the first needle pusher 38, one after another, to further push up the needle stands 28 (e.g., further move the needle stands 28 toward the second casing 14) from the first height. The second positioning surface 40b may be a flat surface contiguous from the second inclined surface 40a, and is configured to position the respective needle stands 28 at a second height. The second height is constant. The first height corresponds to a first protrusion amount h1 (refer to FIGS. 13 and 37). The first protrusion amount h1 refers to a protrusion amount of a needle 26 from the pressing plate 34. The second height corresponds to a second protrusion amount h2 (refer to FIGS. 12 and 36). The second protrusion amount h2 refers to another protrusion amount of a needle 26 from the pressing plate 34. In the first illustrative embodiment, the needle stands 28, the first needle pusher 38 and the second needle pusher 40 may function as a needle moving mechanism 41. The needle moving mechanism 41 is configured to move the respective needles 26 up and down. In the first illustrative embodiment, the second needle pusher 40 is disposed on the first needle pusher 38. Nevertheless, in other embodiments, for example, when viewed from a side facing into the page in FIG. 2, the second needle pusher 40 may be disposed behind or in front of the first needle pusher 38. In such a case, for example, the first needle pusher 38 and the second needle pusher 40 may be plate-like members having respective different heights. That is, the first needle pusher 38 may have any configuration as long as being capable of pushing up the needle stands 28 to the first height, and the second needle pusher 40 may also have any configuration as long as being capable of pushing up the needle stands 28 to the second height.

Figure 10:
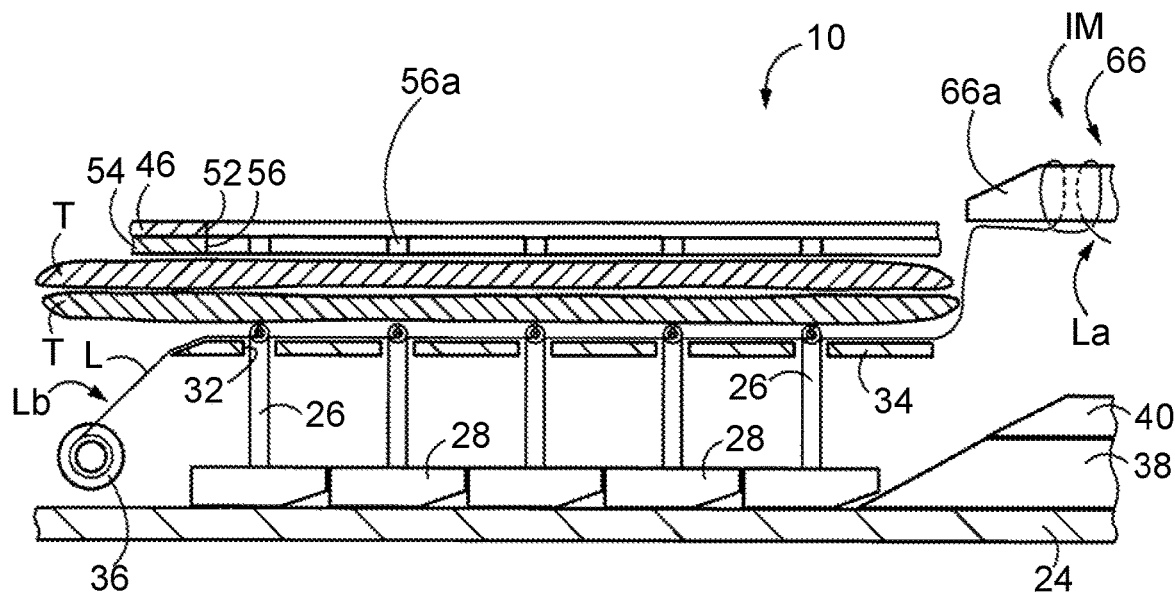
FIG. 10 is a sectional view of the first casing and the second casing of FIGS. 1 and 2 holding therebetween edges of a cut according the first illustrative embodiment of the disclosure.

As illustrated in FIG. 1, the second casing 14 includes a second casing body 48 and a cover plate 50. The second casing body 48 includes a pair of side walls 42 and 44 and a bottom wall 46 that are integral with each other. The side walls 42 and 44 are elongated walls extending parallel to each other. Each of the side walls 42 and 44 has one end and the other end opposite to each other. The other ends of the respective side walls 42 and 44 face the first casing 12 and closer to the first casing 12 than the one ends of the respective side walls 42 and 44 are to the first casing 12. The bottom wall 46 is an elongated wall and connects between the other ends of the side walls 42 and 44. The second casing body 48 has a U-shape in cross section and an open end facing a side opposite to the first casing 12. The cover plate 50 partially covers the open end in a proximal end portion of the second casing body 48. As illustrated in FIG. 2, the bottom wall 46 of the second casing body 48 faces the pressing plate 34 that covers the open end in the distal end portion of the first casing body 30. As illustrated in FIG. 10, the bottom wall 46 also functions as a pressing plate for sandwiching edges of a cut T in cooperation with the pressing plate 34. The bottom wall 46 of the second casing body 48 has a slot 52 having a shape corresponding to a shape of the holes 32 that are connected to each other in the pressing plate 34. The slot 52 allows all of the needles 26 to pass through the bottom wall 46. The second casing 14 further includes a friction plate 54 on a particular surface of the bottom wall 46. The particular surface of the bottom wall 46 faces the pressing plate 34 of the first casing 12. The friction plate 54 may be made of, for example, material having a relatively high friction coefficient such as silicone rubber or may have a surface having a relatively high friction coefficient (e.g., a surface having microscopic asperities) for applying friction to a suture L hooked on a tip portion 26d of each needle 26. The friction plate 54 is adhered to the bottom wall 46. As illustrated in FIG. 10, the friction plate 54 has friction holes 56a and slots 56. The friction holes 56a are positioned in such manner to allow the respective corresponding needles 26 to pass therethrough. In a case where a corresponding needle 26 passes through the friction hole 56a, each of the friction holes 56a slidably contacts particular surfaces of the needle 26. The particular surfaces of the needle 26 may be particular portions of a circumferential wall 26e of the needle 26 and face the side walls 20 and 22, respectively. Each of the slots 56 is disposed between adjacent friction hole 56a and connects between the adjacent friction holes 56a. Each of the friction holes 56a has concave surfaces each having a curvature radius as the same as a radius of a needle 26. This may enable each of the friction holes 56a to slidably contact the particular surfaces of the needles 26.

The second casing 14 further includes a suture hook 60 connected to an operating rod disposed in the tubular member 16. The suture hook 60 is configured to, in a state where the suturing device 10 is closed so that first casing 12 and the second casing 14 are located close to each other, move between a distal-end side position and a proximal-end position in the second casing body 48 along a needle arrangement direction in which the needles 26 are aligned. The suture hook 60 has the same or similar configuration to a latch needle specified in, for example, Japanese Industrial Standard: JIS L 0202. The suture hook 60 includes a hook 62 at its distal end. The hook 62 may be a curved end of the suture hook 60 for catching a suture L. The suture hook 60 further includes a latch 63 (refer to FIG. 15), a butt 64, and a shank 65. The latch 63 is configured to pivot to selectively open and close a mouth of the hook 62. The butt 64 is disposed at a middle portion of the suture hook 60. The shank 65 is disposed at a proximal end of the suture hook 60. As illustrated in FIG. 1, the side wall 42 of the second casing body 48 includes a suture hook guide 42a. The suture hook guide 42a is configured to, in a case where the suture hook 60 is moved forward (e.g., toward the distal end of the second casing 14), guide the butt 64 of the suture hook 60 at a particular rotation angle about an axis of the suture hook 60. More specifically, for example, when the butt 64 is at the particular rotation angle, the hook 62 has a horizontal loop. With such a configuration, the suture hook 60 may move forward (e.g., toward the distal end of the second casing 14) while the hook 62 and butt 64 are each in a horizontal state where the hook 62 has a horizontal loop and the butt 64 extends parallel to the bottom wall 46. In response to the hook 62 having passed the needle 26 that is disposed closest to the distal end of the second casing 14 (hereinafter, also referred to as a frontmost needle 26) among the needles 26, the suture hook 60 is rotated to the right about 90 degrees. This may enable the hook 62 to surely catch a suture L hooked on the needle 26. In a case where the suture hook 60 is moved backward (e.g., toward the proximal end of the second casing 14), the butt 64 is not guided by the suture hook guide 42a and the butt 64 extends perpendicular to the bottom wall 46 and the hook 62 has a vertical loop. Nevertheless, the suture hook 60 might not necessarily be configured to be rotated. That is, the hook 62 may catch a suture L even when the hook 62 is maintained in a certain posture without being rotated. Thus, the rotating configuration might not necessarily be adopted to achieve suturing. FIG. 1 illustrates the butt 64 in both cases where the suture hook 60 is located at the distal-end side position and where the suture hook 60 is located at the proximal-end side position.

The second casing 14 further includes a knot forming jig 66 at the proximal end portion in the second casing body 48. The knot forming jig 66 is elongated and connected to an operating rod disposed in the tubular member 16. The knot forming jig 66 also serves as a jig (e.g., a knot pusher) that pushes a knot to tighten and secure the knot. The knot forming jig 66 is disposed next to the suture hook 60 in a width direction of the second casing 14 and configured to reciprocate along the longitudinal axis of the second casing 14. With this configuration, the knot is tightened and secured by the knot pusher (e.g., the knot forming jig 66), thereby stably maintaining stitches placed in edges of a cut T. As illustrated in FIG. 10, the knot forming jig 66 includes a tapered portion 66a tapered toward its distal end. The knot forming jig 66 has incomplete knots IM at a portion further to a proximal end of the knot forming jig 66 than the tapered portion 66a. The incomplete knots IM are formed by a suture L wound around the knot forming jig 66. In a state where the hook 62 of the suture hook 60 catches a suture L extending from a suture bobbin 36, the hook 62 passes through between a loop of each incomplete knot IM and a side or upper surface of the knot forming jig 66 to make a complete knot M (refer to FIGS. 24 and 25). That is, a complete knot M (refer to FIGS. 24 and 25) is formed by drawing an end of a suture L extending from the suture bobbin 36 through a loop of the incomplete knots IM.

Figure 3:
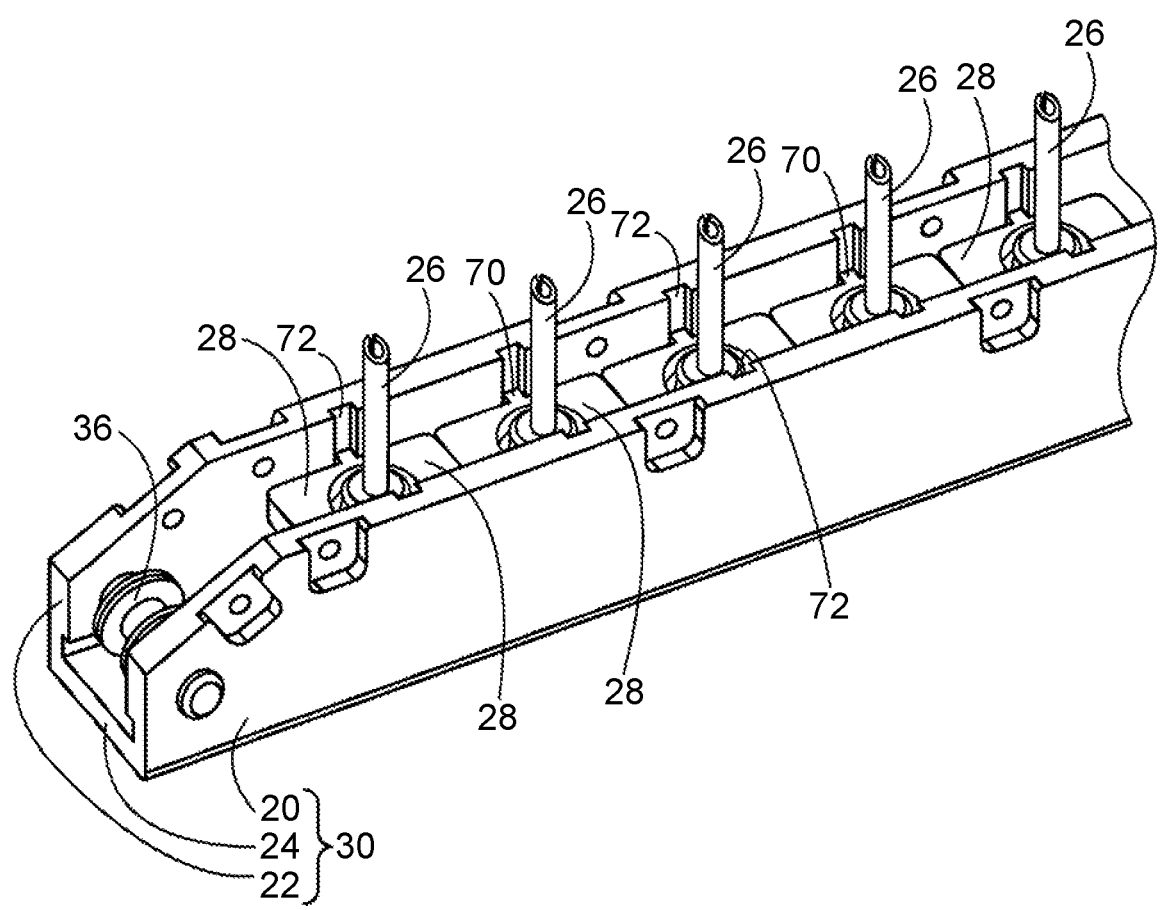
FIG. 3 is a perspective view of the first casing of FIGS. 1 and 2 with a pressing plate and a suture cover removed according the first illustrative embodiment of the disclosure.
Figure 4:
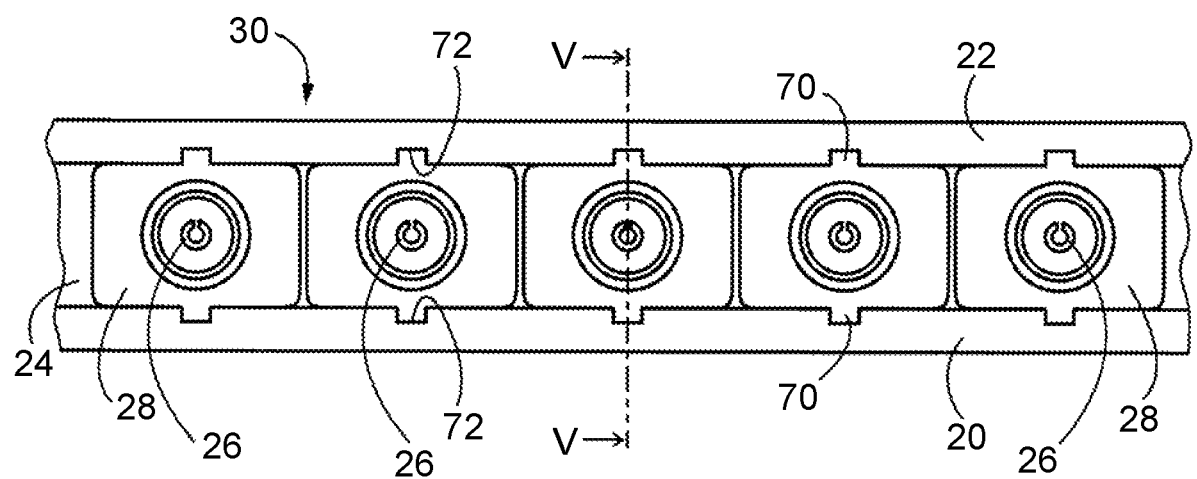
FIG. 4 is a top plan view of the first casing of FIGS. 1 and 2 with the pressing plate and the suture cover removed according the first illustrative embodiment of the disclosure.

FIGS. 3 and 4 are a perspective view and a plan view, respectively, illustrating a state where the needle stands 28 are accommodated in the first casing body 30. In FIGS. 3 and 4, the pressing plate 34 and a suture cover 80 are omitted. The needles 26 stand on the respective needle stands 28 to extend in a direction perpendicular to the respective bottom surfaces 28a of the needle stands 28. As illustrated in FIG. 3, the suture bobbin 36 is disposed at a particular portion further to the distal end of the first casing body 30 than the needle stand 28 on which the frontmost needle 26 stands. The suture bobbin 36 is rotatable in a state where a suitable rotational resistance is applied to the suture bobbin 36 such that a suture L can be drawn from the suture bobbin 36 under appropriate tension.

All the needle stands 28 have the same configuration, and therefore, one of the needle stands 28 will be described in detail. The needle stand 28 has a width slightly narrower than the gap between the side walls 20 and 22 of the first casing body 30. The position of the needle stand 28 in its width direction is fixed by the side walls 20 and 22. The needle stand 28 includes a pair of guide protrusions 70. The guide protrusions 70 protrude toward the side walls 20 and 22, respectively. The side walls 20 and 22 each have guide grooves 72 in their surfaces facing each other. Among the guide grooves 72 of the side walls 20 and 22, guide grooves 72 facing each other are paired. The guide grooves 72 extend in a direction in which the needle 26 extends, that is, in the direction perpendicular to the bottom wall 24. Each pair of the guide grooves 72 is engaged with a corresponding pair of guide protrusions 70 so as to guide a corresponding needle stand 28 to move in the direction perpendicular to the bottom wall 24. The pairs of guide grooves 72 are spaced from each other in the longitudinal axis of the first casing body 30. With this configuration, the needles 26 are spaced from each other at constant intervals along the longitudinal axis of the first casing 12 and extend toward the second casing 14. In the first illustrative embodiment, the plurality of pairs of guide protrusions 70 and the plurality of pairs of guide grooves 72 constitute a needle stand guide 74. As illustrated in FIG. 5, the needle stand 28 has an annular groove 28b that is coaxial with the needle 26. The annular groove 28b is configured to receive one end of a coil spring 78. As illustrated in FIG. 8, the bottom surface 28a of the needle stand 28 includes an inclined surface 28c at one end portion that is closer to the proximal end of the first casing 12, that is, closer to the first needle pusher 38 and the second needle pusher 40. The inclined surface 28c may slidably contact the first inclined surface 38a of the first needle pusher 38 and the second inclined surface 40a of the second needle pusher 40, thereby facilitating moving the needle stand 28. In other embodiments, for example, the needles 26 might not necessarily be spaced apart from each other at constant intervals along the longitudinal axis of the first casing 12.

Figure 6:
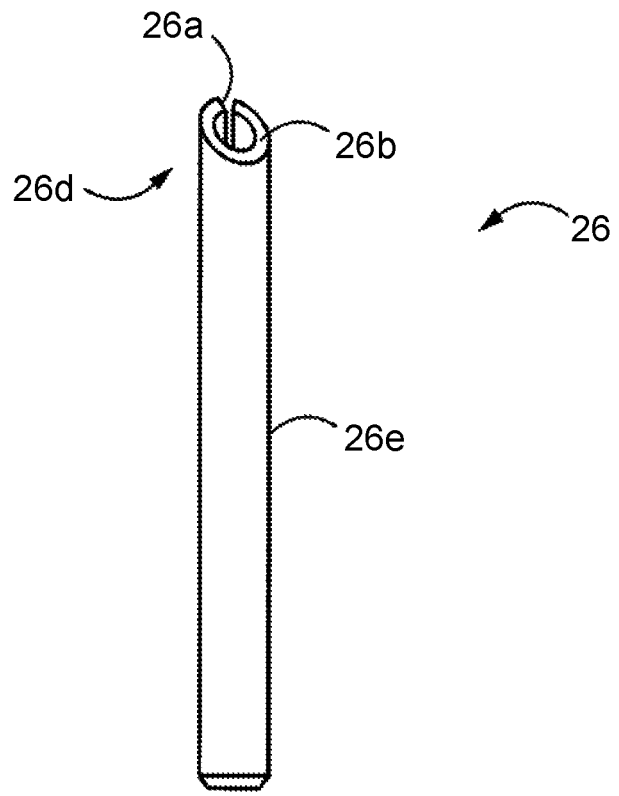
FIG. 6 is a perspective view of a needle standing on one of needle stands according the first illustrative embodiment of the disclosure.
Figure 7:
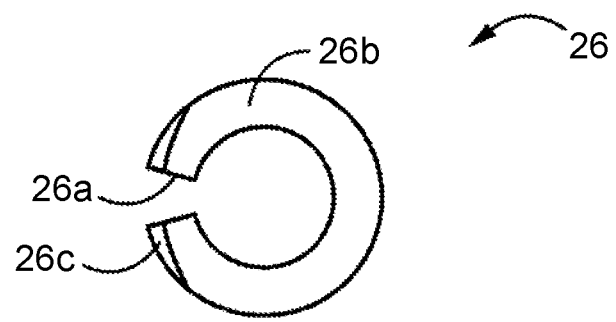
FIG. 7 is an enlarged top plan view of a tip of the needle of FIG. 6 according the first illustrative embodiment of the disclosure.

All the needles 26 have the same configuration, and therefore, one of the needles 26 will be described in detail. As illustrated in FIGS. 6 and 7, the needle 26 may be a metal tube made of stainless steel and have a diameter of 0.6 to 1.0 mm. The needle 26 has a slit 26a in the circumferential wall 26e. The slit 26a extends in an axial direction of the needle 26. The needle 26 has the tip portion 26d that has a bevel cut. Thus, the needle 26 has a bevel 26b such that a particular portion of the needle 26 having the slit 26a serves as an acute angled tip of the needle 26. That is, the slit 26a extends in parallel to the axis of the needle 26 along the axial direction of the needle 26 from a point to an opposite end of the needle 26. As illustrated in FIG. 7, the needle 26 has chamfered surfaces 26c at its tip end. The slit 26a has a width slightly greater than an outside diameter of a suture L. Nevertheless, the slit 26a might not necessarily extend from an end (e.g., the point) to the other end in the axial direction of the needle 26 as long as the needle 26 can hold a suture L at its tip. In other embodiments, for example, the slit 26a may have a length corresponding to a length of the bevel 26b of the needle 26 in the axial direction of the needle 26.

As illustrated in FIGS. 5 and 8, the first casing 12 accommodates coil springs 78. Each coil spring 78 is disposed between an inner surface of the pressing plate 34 and an annular groove 28b of a corresponding needle stand 28 while a certain preload is applied to each coil spring 78. The pressing plate 34 is fixed to the first casing body 30 to close the open end of the first casing body 30. Although the needles 26 are retracted in the first casing 12 at all times, such a configuration may allow the needles 26 to protrude from the pressing plate 34 one after another in increasing order of distance from the proximal end of the first casing 12 in response to the first needle pusher 38 and the second needle pusher 40 moving forward toward the distal end of the first casing 12. In addition, such a configuration may retract the needles 26 below the pressing plate 34 one after another in ascending order of distance from the proximal end of the first casing 12 due to urging forces of the respective coil springs 78 in response to the first needle pusher 38 and the second needle pusher 40 moving backward toward the proximal end of the first casing 12. FIG. 8 illustrates a state where the needle stand 28 disposed closest to the proximal end of the first casing 12 among the needle stands 28 is pushed up by the first inclined surface 38a of the first needle pusher 38. In other embodiments, for example, the needles 26 may be configured to be retracted below the pressing plate 34 by their own weights. In such a case, the coil springs 78 might not necessarily be provided. In still other embodiments, an urging force applied to each needle stand 28 may be generated by another suitable configuration other than the coil spring.

Figure 9:
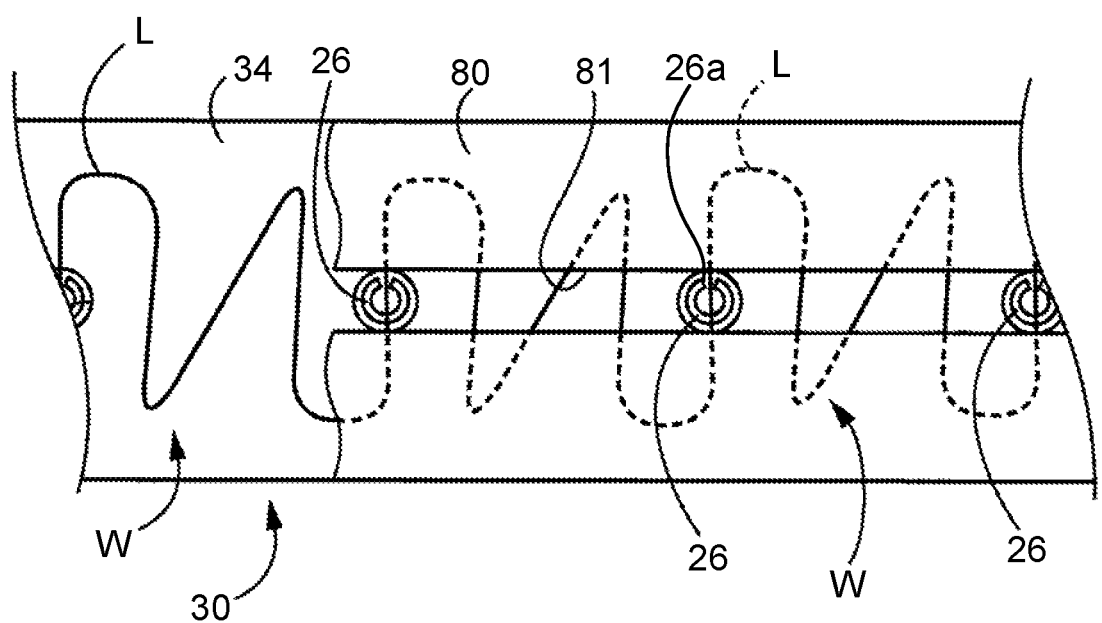
FIG. 9 is a top plan view of the first casing of FIGS. 1 and 2 for explaining routing of a suture held by needles slightly protruding through the suture cover according to the first illustrative embodiment of the disclosure.

FIG. 9 illustrates how a suture L hooked on the tips of the needles 26 slightly protruding relative to the pressing plate 34 prior to suturing of edges of a cut T is routed on the pressing plate 34.

The suture bobbin 36 has a suture L wound therearound. The suture L extends from the suture bobbin 36 and is placed in the slit 26a of the needle 26 disposed at a certain position of the first casing body 30, for example, the frontmost needle 26. The suture L further extends to the needle 26 next to the frontmost needle 26 in the needle arrangement direction to be placed in the slit 26a of the second frontmost needle 26. The suture L has a certain loosened portion W between the needles 26. For example, the loosened portion W is routed to form a W shape so as not to get tangled. The pressing plate 34 may further include small protrusions for guiding routing of the suture L to form certain loosened portions W between needles 26. A loosened portion W has a length twice or more as long as the second protrusion amount h2 of a needle 26 relative to the pressing plate 34. As illustrated in FIG. 9, the suture L on the pressing plate 34 extending between the slits 26a of the needles 26 is covered with a suture cover 80 to reduce slippage of the loosened portions W in the suture L from the pressing plate 34. The suture cover 80 has a slot 81 having a shape corresponding to a shape of the holes 32 that are connected to each other, similar to the slots 52 and 56. In a case where a solid oil such as grease is applied to a surface of the pressing plate 34 to reduce slippage of the loosened portions W in the suture L from the pressing plate 34, the suture cover 80 may be omitted. In FIGS. 8 and 10, and subsequent figures, the suture cover 80 is omitted from the drawings.

Referring to FIGS. 10 to 25, a description will be provided on a procedure to stitch edges of a cut T with a suture L using the suturing device 10.

The suturing device 10 is opened to increase a distance between the first casing 12 and the second casing 14 and is placed at an appropriate position so that the first casing 12 and the second casing 14 are located on opposite sides of edges of a cut T. FIG. 10 illustrates this state. In this state, a suture L is held by the tips of the needles 26 via the respective slits 26a while the suture L has loosened portions W between the tips of the respective adjacent needles 26 (refer to FIG. 9). The suture L extending from the suture bobbin 36 has an end portion La that is located opposite to the suture bobbin 36 with respect to the plurality of needles 26 or stitches N. The end portion La of the suture L is wound around the knot forming jig 66 to form incomplete knots IM. That is, FIG. 10 illustrates a preliminary preparation step.

Figure 11:
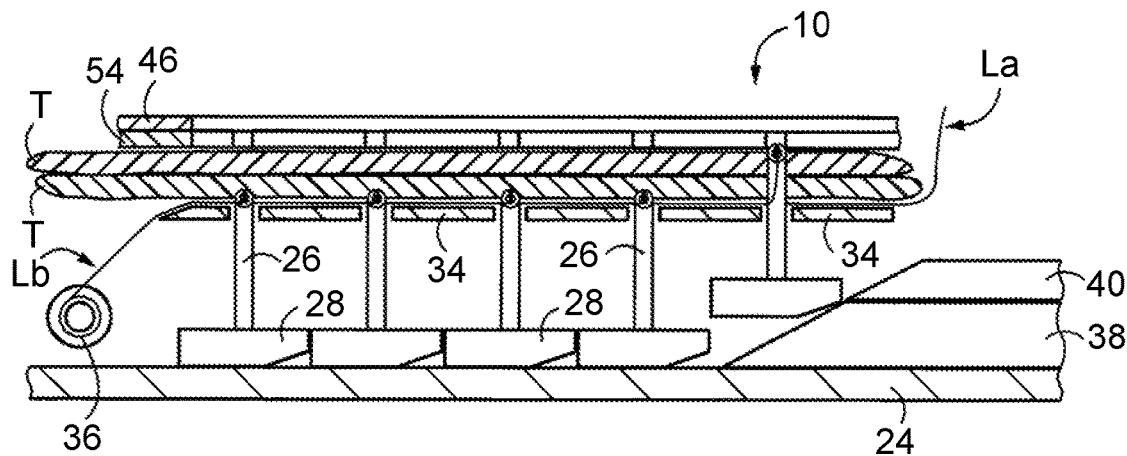
FIG. 11 illustrates a state where a first needle pusher and a second needle pusher push up one of the needles by their forward movement from their positions of FIG. 10 according the first illustrative embodiment of the disclosure.

Thereafter, the suturing device 10 is closed to decrease the distance between the first casing 12 and the second casing 14, thereby sandwiching and holding the edges of the cut T between the first casing 12 and the second casing 14. FIG. 11 illustrates this state. Then, in response to the first needle pusher 38 and the second needle pusher 40 being started to be moved forward toward the distal end of the first casing 12 (hereinafter, such movement is also simply referred to as a forward movement), the needles 26 start to protrude one after another from the pressing plate 34. That is, FIG. 11 illustrates a sandwiching step.

Figure 12:
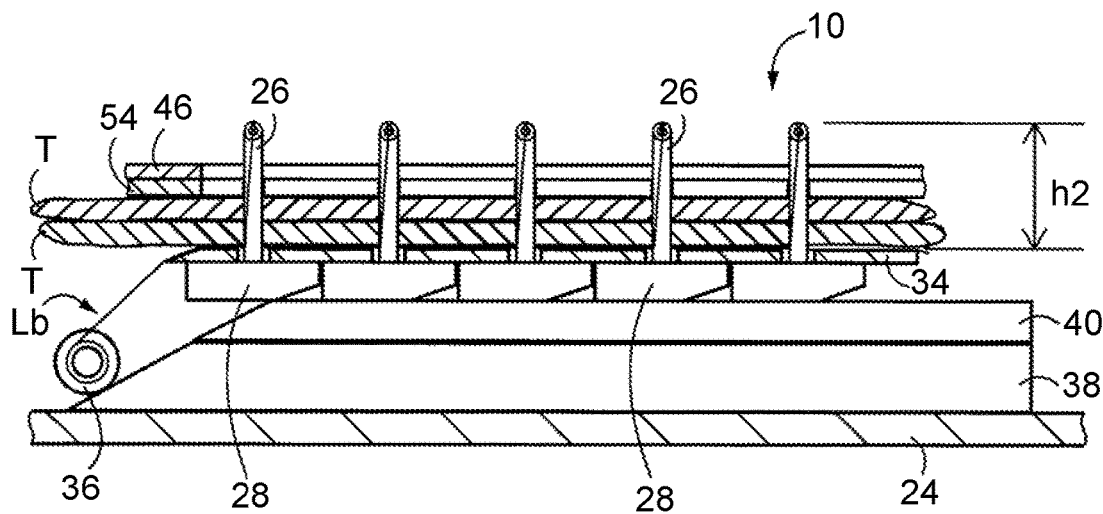
FIG. 12 illustrates a state where the first needle pusher and the second needle pusher push up all of the needles by their further forward movement from their positions of FIG. 11 to according the first illustrative embodiment of the disclosure.

As the first needle pusher 38 and the second needle pusher 40 are respectively moved forward toward the distal end of the first casing 12, as illustrated in FIG. 12, the needle stands 28 are pushed up one after another and located at the second height where the needle stands 28 are on the second positioning surface 40b of the second needle pusher 40. Thus, all the needles 26 protrude from the pressing plate 34 by the second protrusion amount h2. In response to the needles 26 protruding from the pressing plate 34, the needles 26 penetrate the edges of the cut T and pass through the respective friction holes 56a of the friction plate 54 adhered to the bottom wall 46 of the second casing 14 and the slot 52 of the bottom wall 46 of the second casing 14. FIG. 12 illustrates such a needle penetration step.

Figure 13:
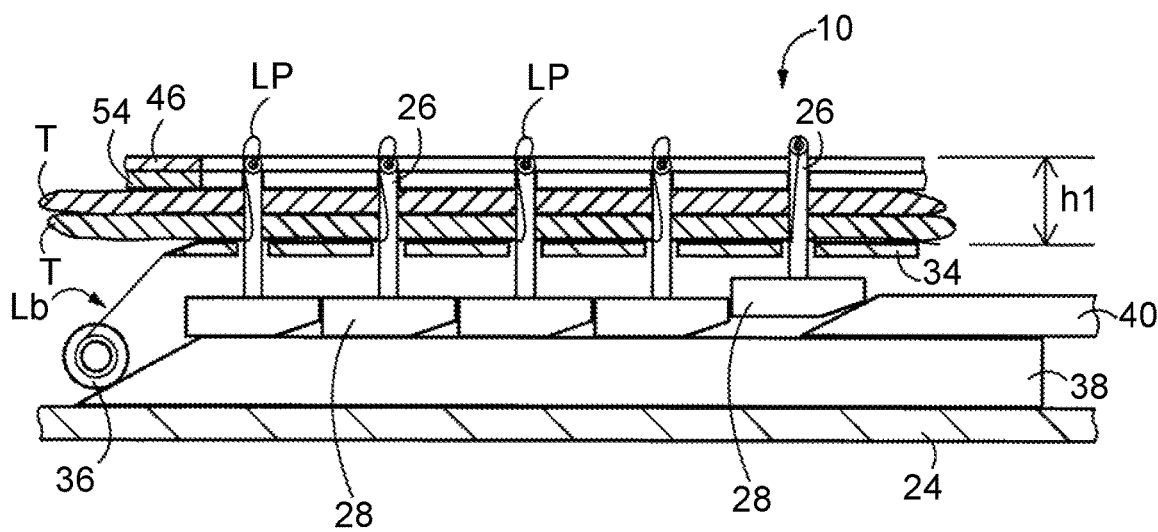
FIG. 13 illustrates a state where a loop is formed at a tip of one or more of the needles by backward movement of the second needle pusher from the position of FIG. 12 according the first illustrative embodiment of the disclosure.

As the second needle pusher 40 is moved backward toward the proximal end of the first casing 12 (hereinafter, such movement is also simply referred to as a backward movement), as illustrated in FIG. 13, the needle stands 28 are moved downward one after another and thus located at the first height where the needle stands 28 are on the first positioning surface 38b of the first needle pusher 38. That is, the needles 26 are lowered to be partially retracted below the pressing plate 34 so that the needles 26 protrude from the pressing plate 34 by the first protrusion amount h1. In such a needle lowering step, a loop LP is formed at the tip portion 26d of each needle 26 by friction caused between the suture L held by the tip of the needle 26 via the slit 26a and the friction plate 54. FIG. 13 illustrates such a loop forming step. Each loop LP is oriented perpendicular to a plane extending in a direction in which the suture hook 60 is moved forward.

Figure 14:
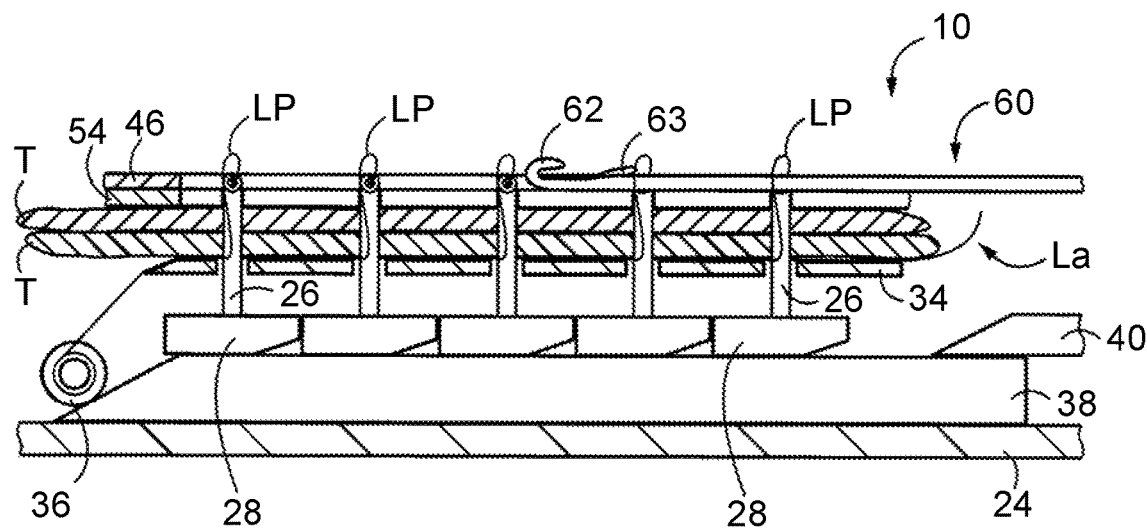
FIG. 14 illustrates a state after the state of FIG. 13, illustrating the state in which a suture hook is inserted into the loops formed at the tips of the needles one after another by forward movement of the suture hook according the first illustrative embodiment of the disclosure.
Figure 15:
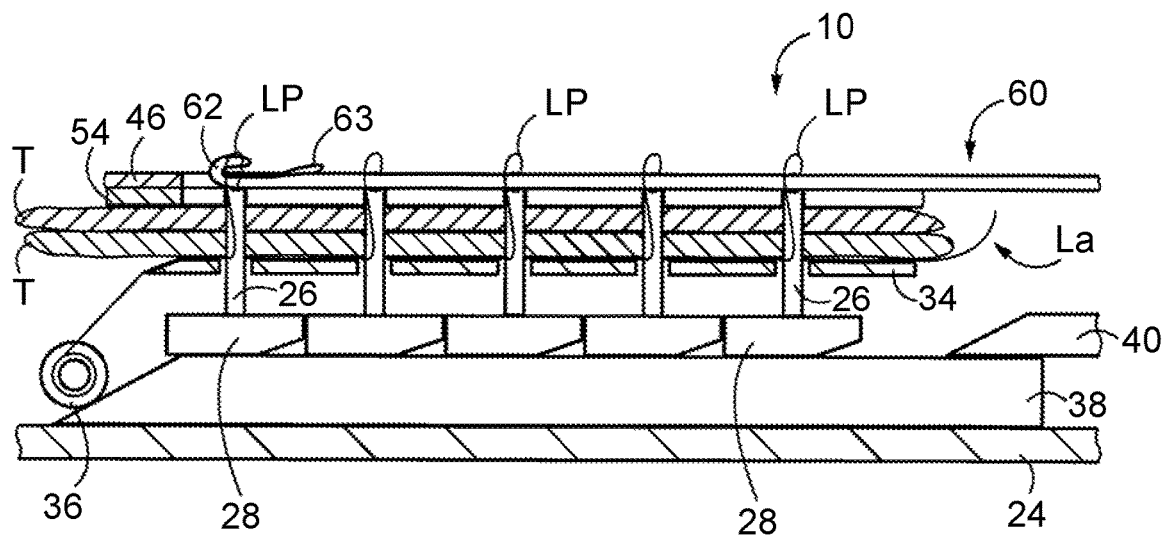
FIG. 15 illustrates a state after the state of FIG. 14, illustrating the state in which the suture hook has reached a furthest position by its further forward movement from the position of FIG. 14 according the first illustrative embodiment of the disclosure.

The suture hook 60 is disposed in the second casing 14 at the position to pass through each of such loops LP. As the suture hook 60 is moved forward toward the distal end of the second casing 14, the hook 62 disposed at the distal end of the suture hook 60 passes through, one after another, the loops LP formed at the tips of the respective needles 26. FIGS. 14 and 15 illustrate a suture hook insertion step. More specifically, for example, FIG. 14 illustrates a state where the suture hook 60 is being moved forward toward the distal end of the second casing 14 and FIG. 15 illustrates a state where the suture hook 60 has reached the farthest position in the forward movement of the suture hook 60.

While the suture hook 60 is moved forward, the latch 63 is kept tilted toward the proximal end of the second casing 14 to open the mouth of the hook 62. While the suture hook 60 is moved forward in such a state, the butt 64 of the suture hook 60 is guided by the suture hook guide 42a. Thus, the hook 62 of the suture hook 60 is moved forward while being oriented extending parallel to the bottom wall 46. Although the hook 62 is oriented as such in actual case, for ease of understanding, FIGS. 14 and 15 illustrates the hook 62 oriented extending perpendicular to the bottom wall 46.

Figure 16:
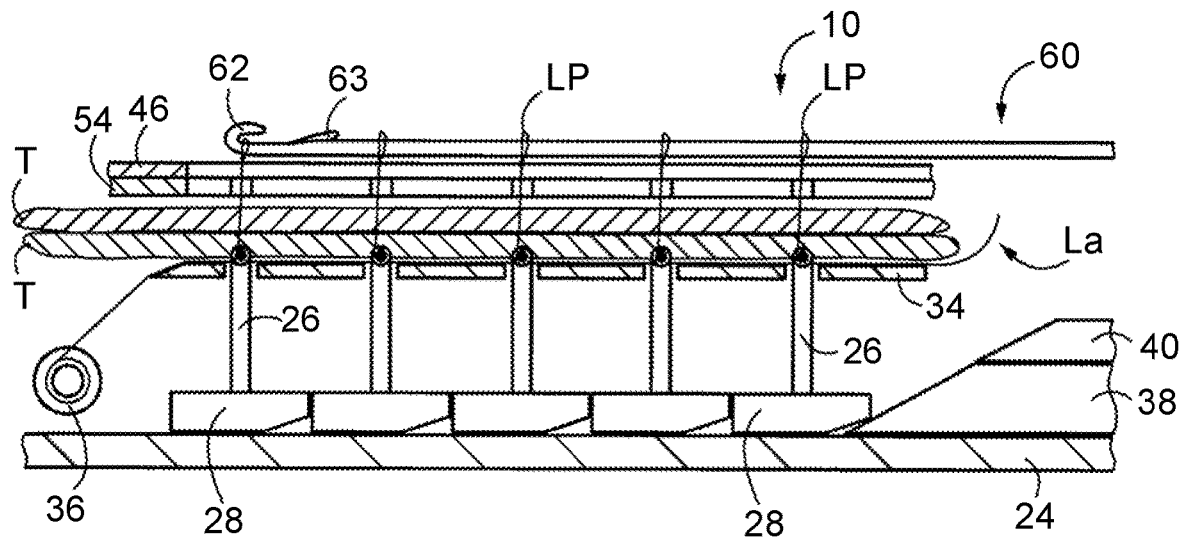
FIG. 16 illustrates a state after the state of FIG. 15, illustrating the state in which the needles are positioned at a lower position by backward movement of the first needle pusher whereby the needles are pulled out from the edges of the cut according the first illustrative embodiment of the disclosure.
Figure 17:
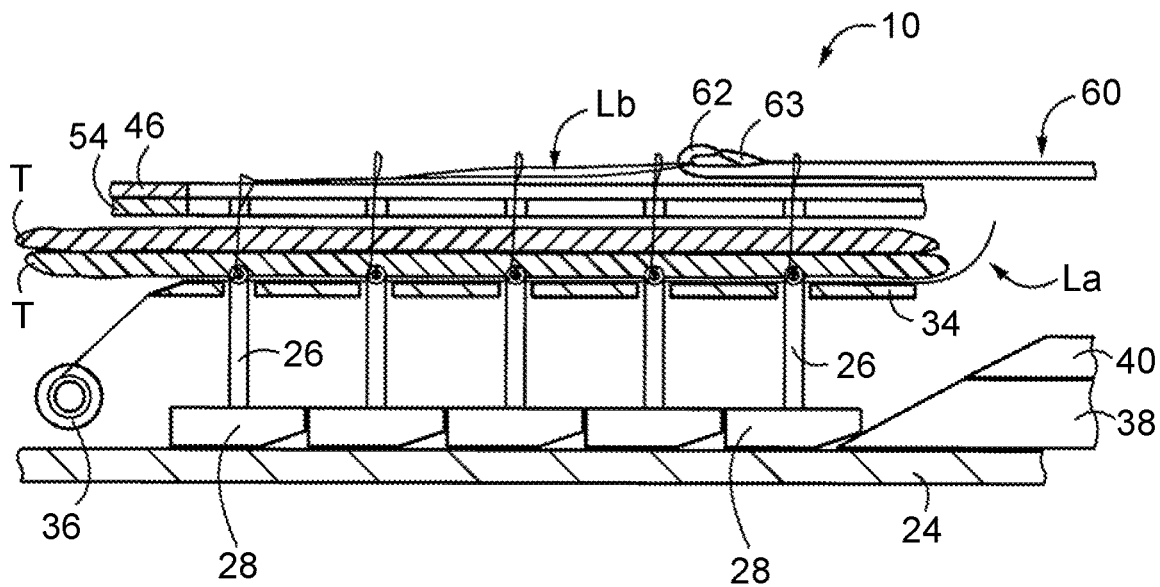
FIG. 17 illustrates a state where the suture hook engaging the loop formed at the tip of the needle positioned closest to a distal end of the first casing is moved backward from the position of FIG. 16 according the first illustrative embodiment of the disclosure.
Figure 18:
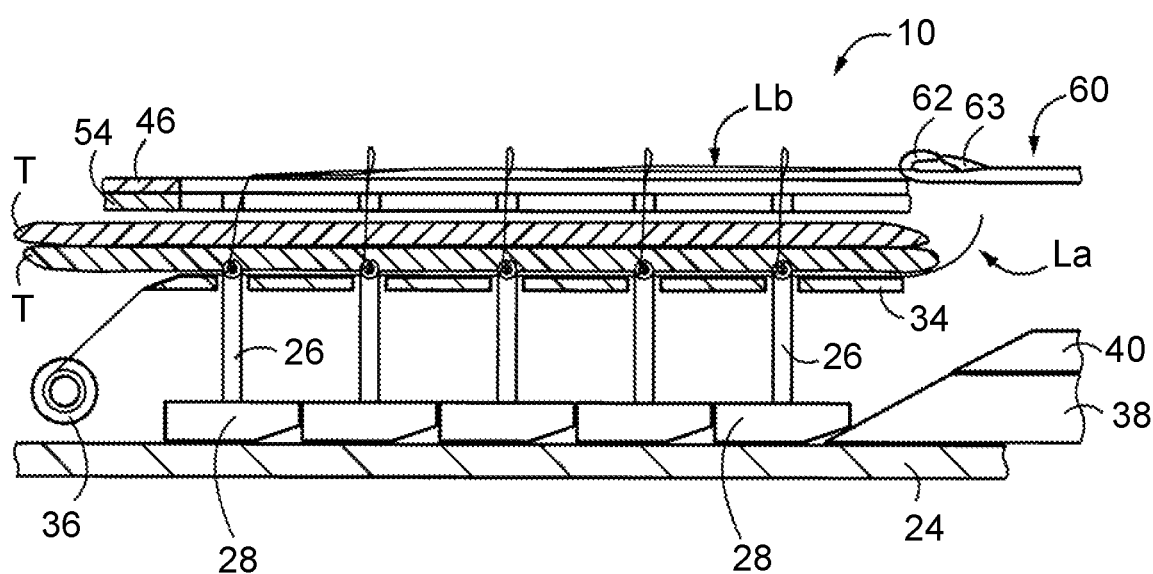
FIG. 18 illustrates a state after the state of FIG. 17, illustrating the state in which the suture hook is retracted according the first illustrative embodiment of the disclosure.

As the first needle pusher 38 is moved backward toward the proximal end of the second casing 14, the needle stands 28 are moved downward one after another and thus located on the bottom wall 24 of the first casing 12. That is, in response to the needle stands 28 being lowered to such a position, the needles 26 are further retracted below the pressing plate 34 so that the needles 26 are removed from the edges of the cut T. FIGS. 16, 17, and 18 illustrate a needle removal step. In the needle removal step, the suture hook 60 is moved backward while the hook 62 and the butt 64 of the suture hook 62 are oriented extending perpendicular to the bottom wall 46. As illustrated in FIGS. 17 and 18, while the suture hook 60 is moved backward, the mouth of the hook 62 of the suture hook 60 is closed by the latch 63. Thus, after the hook 62 catches the loop LP formed at the tip of the frontmost needle 26, the suture hook 60 is moved backward without catching the other loops LP formed at the remaining needles 26. In such a suture hook retracting step, the suture L is drawn from the suture bobbin 36. The suture L has another end portion Lb that is located, in a suturing preparation step, on the same side where the suture bobbin 36 is provided, with respect to the plurality of needles 26 or stitches N. In FIGS. 17 and 18, the suture L that has been drawn from the suture bobbin 36 by the suture hook 60 and threaded or is to be threaded through the loops LP may be an end portion Lb of the suture L.

Figure 19:
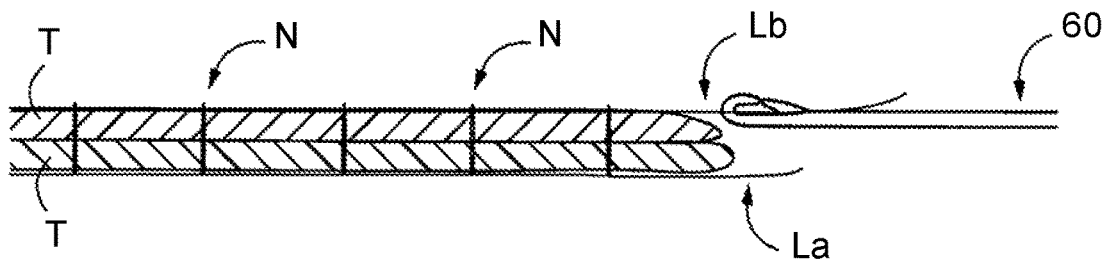
FIG. 19 is an explanatory view for explaining a procedure of ligating the edges of the cut in the state of FIG. 18 in which the first casing and the second casing are omitted according the first illustrative embodiment of the disclosure.

Then, a knot M is formed as described below on the end portions La and Lb of the suture L that form stitches N placed in the edges of the cut T by suturing (refer to FIG. 19). Referring to FIGS. 19 to 25, a description will be provided on a procedure to form the knot M. In FIGS. 19 to 25, for convenience of description, the components, members or portions other than the edges of the cut T, the suture hook 60, and the knot forming jig 66 may be omitted.

Figure 20:
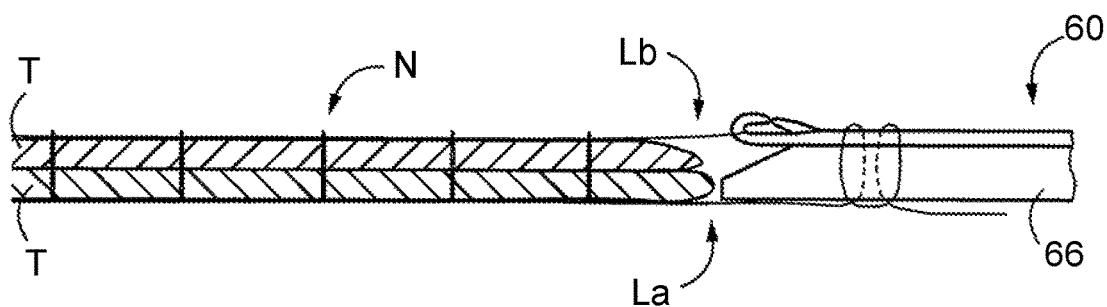
FIG. 20 is an explanatory view illustrating a state after the state of FIG. 19, illustrating the state in which a knot forming jig having incomplete knots formed therearound is located adjacent to the edges of the cut and the suture hook passes through a space between the knot forming jig and each of the incomplete knots according the first illustrative embodiment of the disclosure, wherein the incomplete knots are formed by an end portion of a suture being wound around the knot forming jig.
Figure 21:
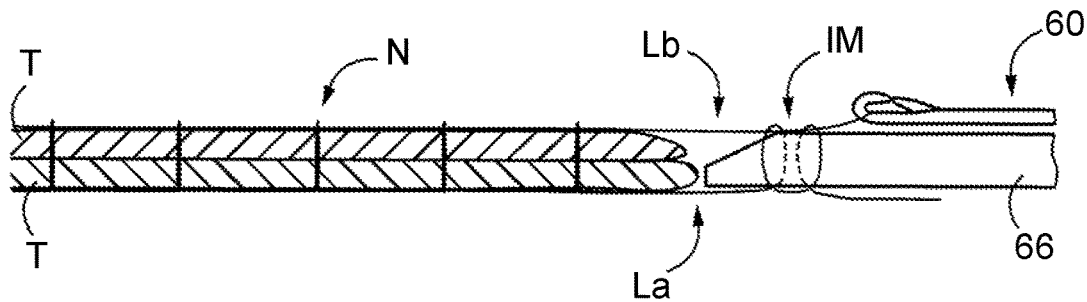
FIG. 21 illustrates a state after the state of FIG. 20, illustrating the state in which the suture hook is pulled out by its backward movement from between the knot forming jig and each of the incomplete knots according the first illustrative embodiment of the disclosure.
Figure 22:
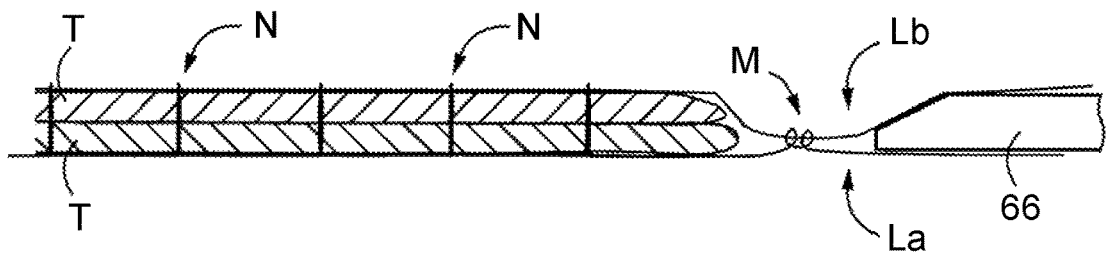
FIG. 22 illustrates a state after the state of FIG. 21, illustrating the state in which the suture hook is further moved backward and the knot forming jig is also moved backward according the first illustrative embodiment of the disclosure.
Figure 23:
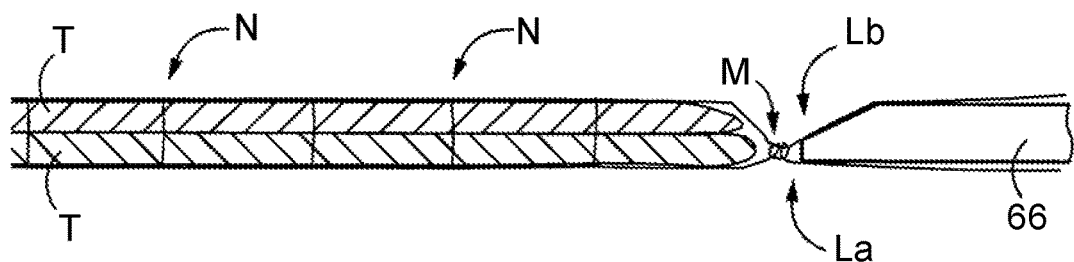
FIG. 23 illustrates a state after the state of FIG. 22, illustrating the state in which a knot formed from the incomplete knots is firmly tightened by the knot forming jig that is moved forward while the suture is tightened according the first illustrative embodiment of the disclosure.
Figure 24:
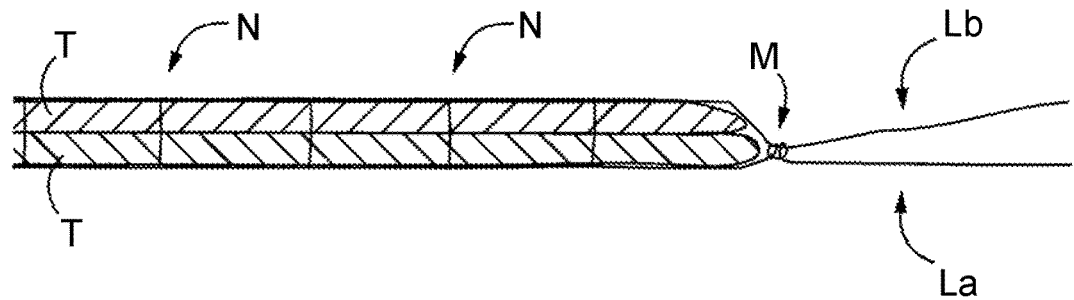
FIG. 24 illustrates a state after the state of FIG. 23, illustrating the state in which the knot forming jig is retracted by its further backward movement according the first illustrative embodiment of the disclosure.
Figure 25:
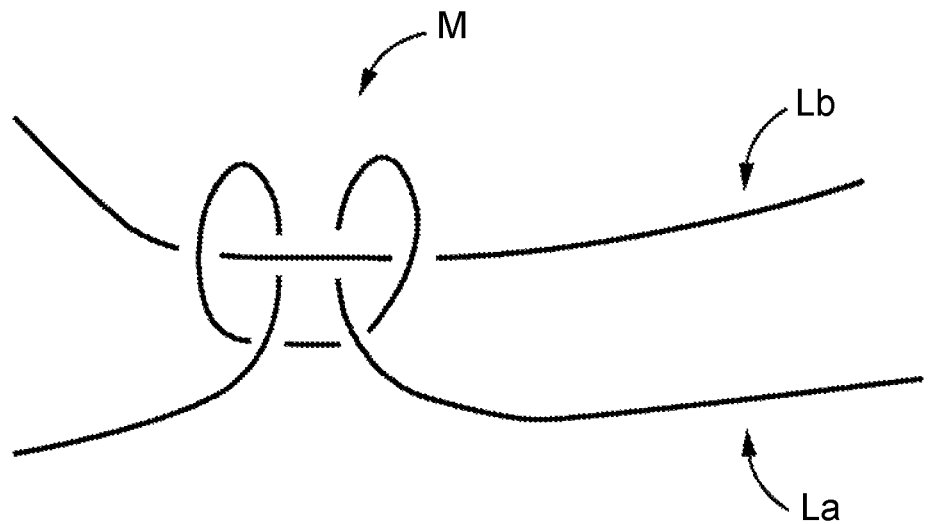
FIG. 25 is an enlarged view of a base form of one example of the knot (e.g., a square knot) formed in FIG. 24 according the first illustrative embodiment of the disclosure.
Figure 26:
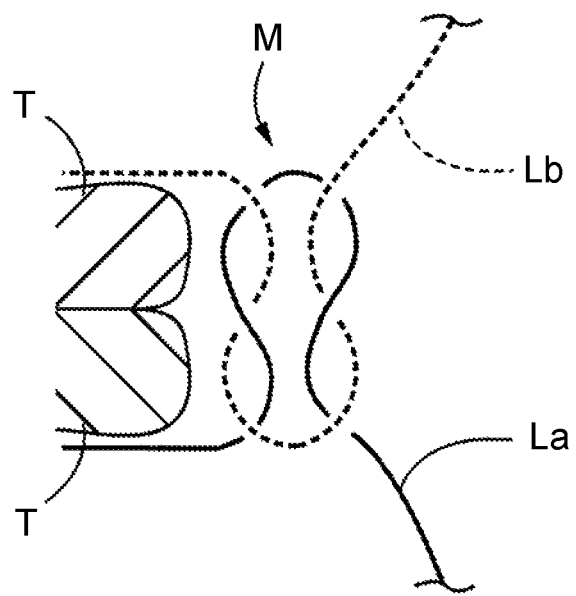
FIG. 26 illustrates a structure of the square knot formed from the base form of the knot of FIG. 25 with the knot loosened for easy understanding according the first illustrative embodiment of the disclosure.

In response to tension being applied to the end portion La of the suture L in the state of FIG. 18 to tighten the suture L, as illustrated in FIG. 19, the loops LP become smaller in size and disappear. Thus, the edges of the cut T is sutured in a certain tightened state. Then, as the knot forming jig 66 is moved forward toward the distal end of the second casing 14 while tension is applied to the end portion La of the suture L, as illustrated in FIG. 20, incomplete knots IM preformed using the suture L on the distal end portion of the knot forming jig 66 and the suture hook 60 are moved toward the edges of the cut T. The incomplete knots IM have been formed by winding the suture L around the knot forming jig 66 and the suture hook 60. Thereafter, in response to the suture hook 60 being pulled from the incomplete knots IM by its further backward movement in such a state, the state of FIG. 20 shifts to a state of FIG. 21. In response to the knot forming jig 66 being then pulled from the incomplete knots IM by its backward movement, the state of FIG. 21 shifts to the state of FIG. 22. Thus, a loose knot M is formed. After that, as illustrated in FIG. 23, the end portions La and Lb of the suture L are both tightened in a state where the knot forming jig 66 has been moved forward from the state of FIG. 22, thereby obtaining an original shape of the knot M as illustrated in FIG. 24. FIG. 25 is an enlarged view illustrating an original shape of the knot M. FIG. 26 is an enlarged view illustrating the tightened knot M obtained by tightening the knot M of FIG. 25. For example, the knot M of FIG. 25 is a square knot.

Figure 27:
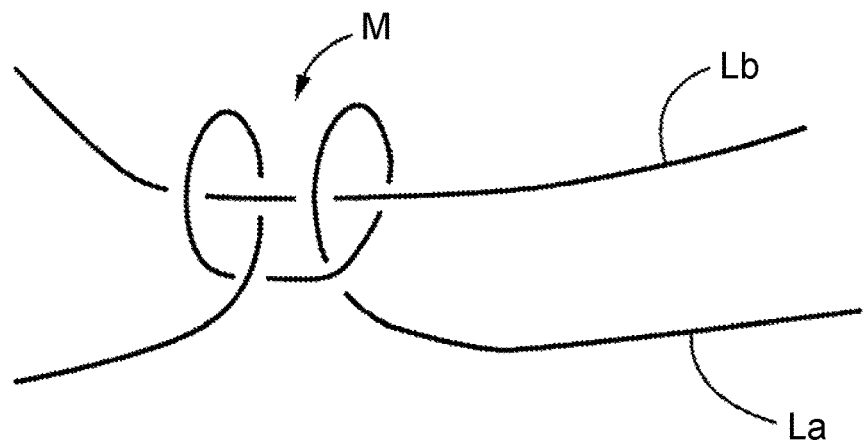
FIG. 27 is an enlarged view of a base shape of another example of the knot (e.g., a granny knot) formed in FIG. 24 according the first illustrative embodiment of the disclosure.
Figure 28:
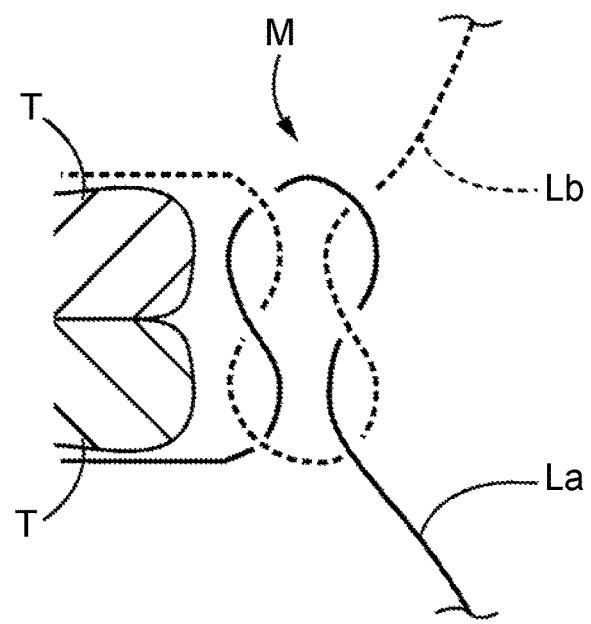
FIG. 28 illustrates a structure of the granny knot formed from the base form of the knot of FIG. 27 with the knot loosened for easy understanding according the first illustrative embodiment of the disclosure.

In another example, another type of the knot M may be obtained by changing the winding direction of the suture L that forms the incomplete knots IM obtained by winding the end portion La of the suture L around the knot forming jig 66. FIG. 27 is an enlarged view illustrating an original shape of another type of the knot M. FIG. 28 is an enlarged view illustrating the tightened knot M obtained by tightening the knot M of FIG. 27. For example, the knot M of FIG. 27 is a granny knot.

According to the first illustrative embodiment, the suturing device 10 includes the first casing 12, the second casing 14, the needles 26, the needle moving mechanism 41, and the suture hook 60. The first casing 12 and the second casing 14 are configured to move toward and away from each other to sandwich therebetween edges of a cut T. The needles 26 are disposed at the first holding member and aligned in the needle arrangement direction with their points pointing to the second casing 14. The needles 26 are configured to hold a suture L at tips thereof and penetrate the edges of the cut T. The needle moving mechanism 41 is configured to move the needles 26 toward the second casing 14, thereby allowing the needles 26 holding the suture L at the respective tips to penetrate the edges of the cut T. The suture hook 60 is disposed at the second casing 14. The suture hook 60 is configured to move along the needle arrangement direction to catch the suture L that has reached the second casing 14 via the edges of the cut T by movement of the needles 26 toward the second casing 14 by the needle moving mechanism 41. With this configuration, in a state where the first casing 12 and the second casing 14 that have been moved toward each other sandwich therebetween the edges of the cut T, the needle moving mechanism 41 moves, toward the second casing 14, the needles 26 that is disposed at the first casing 12 and holds the suture L at their tips. In response to this, the needles 26 penetrates the edges of the cut T, thereby allowing the tip portions of the needles 26 to reach the second casing 14 via the edges of the cut T. Thereafter, in response to the suture hook 60 being moved along the needle arrangement direction in such a state, the suture L that has reached the second casing 14 via the edges of the cut T is caught by an end portion Lb of the suture L threaded through the distal end portion of the suture hook 60. Consequently, stitches N may be placed in the edges of the cut T readily and securely by a mechanical action achieved by a simple operation. According to the suturing device 10, a length of a series of stitches N (e.g., a width of a stitching range) may be adjusted by changing which of the loops LP formed at the tips of the needles 26 is caught by the suture hook 60.

According to the suturing device 10 of the first illustrative embodiment, the needles 26 are arranged at equal intervals. Such a needle arrangement may enable stitches N to be placed in edges of a cut T at equal pitches, thereby achieving an appropriate suturing strength.

According to the suturing device 10 of the first illustrative embodiment, each of the needles 26 has a slit 26a defined in at least the tip portion of the needle 26. The slit 26a is configured to allow the needle 26 to releasably hold the suture L at the tip of the needle 26. The slit 26a extends in the tip portion of each of the needle 26 along the direction intersecting with the needle arrangement direction, that is, the direction in which the suture hook 60 moves. With this configuration, loops LP may be formed using the suture L held by the tip portions of the respective needles 26 via the respective slits 26a such the loops LP are oriented in a particular direction to allow the suture hook 60 to be readily inserted thereinto, thereby surely suturing edges of a cut T.

According to the suturing device 10 of the first illustrative embodiment, each of the needles 26 has the acute angled tip and the circumferential wall 26e. In each of the needles 26, the slit 26a extends in at least a particular portion of the circumferential wall 26e along the axial direction of the needle 26 from the point of the acute angled tip to the proximal end of the needle 26 opposite to the acute angled tip in the axial direction of the needle 26. The particular portion of the circumferential wall 26e extends from the point of the acute angled tip of the needle 26. Such a configuration may thus enable each of the needles 26 to have a relatively high holding force for holding the suture L at their tips. Thus, the needles 26 may stably hold loops LP formed using the suture L at their tips, thereby securely suturing edges of a cut T.

According to the first illustrative embodiment, the suturing device 10 includes at least one needle stand 28 supporting the proximal ends of the needles 26 with the points of the needles 26 pointing to the second casing 14. The needle moving mechanism 41 is further configured to move the at least one needle stand 28 toward the second casing 14. With this configuration, in response to the needles 26 being moved toward the second casing 14 by the needle moving mechanism 41, the needles 26 penetrate edges of a cut T sandwiched by the first casing 12 and the second casing 14, thereby allowing the tip portions of the needles 26 to reach the second casing 14 via the edges of the cut T.

According to the suturing device 10 of the first illustrative embodiment, the at least one needle stand 28 includes a plurality of needle stands 28 each supporting a proximal end of a corresponding needle 26. With this configuration, the needles 26 may be caused by the needle moving mechanism 41 to penetrate edges of a cut T one after another.

According to the suturing device 10 of the first illustrative embodiment, the first casing 12 includes the needle stand guide 74 configured to guide movement of the needle stands 28 in such a manner to restrict the needle stands 28 from moving in the needle arrangement direction and allow the needle stands 28 to move toward the second casing 14. With this configuration, the needles 26 may be caused by the needle moving mechanism 41 to penetrate edges of a cut T sandwiched by the first casing 12 and the second casing 14 while maintaining the intervals between the needles 26.

According to the suturing device 10 of the first illustrative embodiment, the needle moving mechanism 41 includes a pusher (e.g., the first needle pusher 38 and the second needle pusher 40) configured to move along the needle arrangement direction. The pusher is further configured to move the needles 26 toward the second casing 14 to protrude from the first casing 12 by engaging the leading end of the pusher with the needle stands 28. Thus, the needles 26 may be caused by the pusher to penetrate edges of a cut T sandwiched by the first casing 12 and the second casing 14.

According to the suturing device 10 of the first illustrative embodiment, the needle moving mechanism 41 includes the first needle pusher 38 and the second needle pusher 40. The first needle pusher 38 is disposed at the first casing 12 and configured to move along the longitudinal axis of the first casing 12. The first needle pusher 38 has the first inclined surface 38a and the first positioning surface 38b. The first inclined surface 38a is configured to, by engaging the needle stands 28 one after another, move the needles 26 toward the second casing 14 to protrude from the first casing 12. The first positioning surface 38b is a flat surface contiguous from the first inclined surface 38a and is configured to position the needle stands 28 at the first height. The second needle pusher 40 is disposed at the first casing 12 and configured to move along the longitudinal axis of the first casing 12. The second needle pusher 40 has the second inclined surface 40*a* and the second positioning surface 40*b*. The second inclined surface 40*a* is configured to, by engaging, one after another, the needle stands 28 that have been moved toward the second casing 14 by the first needle pusher 38, move the needles 26 toward the second casing 14 to further protrude from the first casing 12. The second positioning surface 40*b* is a flat surface contiguous from the second inclined surface 40*a* and is configured to position the needle stands 28 at the second height. With this configuration, the needles 26 are moved toward the second casing 14 (e.g., pushed up) to protrude from the first casing 12 by the second protrusion amount h2 via edges of a cut T sandwiched by the first casing 12 and the second casing 14 and then moved toward the first casing 12 (e.g., lowered) to protrude from the first casing 12 by the first protrusion amount h1. Such a needle movement may achieve forming of loops LP at the tips of the respective needles 26.

According to the suturing device 10 of the first illustrative embodiment, the needle moving mechanism 41 includes the return springs (e.g., the coil springs 78) configured to urge the needle stands 28 toward the first casing 12. With such a configuration, the needles 26 penetrating edges of a cut T sandwiched by the first casing 12 and the second casing 14 may be removed therefrom by urging force of the return springs and positioned in the first casing 12.

The suturing device 10 according to the first illustrative embodiment includes the knot forming jig 66 disposed at the proximal end portion of the second casing 14. The suture hook 60 is disposed at the proximal end portion of the second casing 14 in such a manner to move along the needle arrangement direction. The knot forming jig 66 has an elongated shape. The end portion La of the suture L is wound around the knot forming jig 66 in advance to form a loop in the suture L for forming a certain knot M. The suture hook 60 around which the end portion Lb of the suture L is wound passes through between the loop of the wound end portion La and the knot forming jig 66 to allow the knot forming jig 66 to form the certain knot M in the suture L held by the suture hook 60. With this configuration, a knot M may be formed by tying an end portion Lb of the suture L and an end portion La of the suture L, thereby stably fastening stitches N placed in edges of a cut T. The end portion Lb may extend from the suture L forming loops LP at the tips of the respective needles 26 and passing through the loops LP together with the suture hook 60. The end portion La of the suture L may be wound around the knot forming jig 66.

According to the suturing device 10 of the first illustrative embodiment, the knot forming jig 66 is configured to move along the longitudinal axis of the second casing 14. With this configuration, in forming of a knot M, the knot forming jig 66 may be readily pulled out from the loop of the end portion La of the suture L would around the knot forming jig 66.

According to the suturing device 10 of the first illustrative embodiment, the first casing 12 includes the suture bobbin 36 around which an end portion Lb of the suture L is wound therearound to hold the suture L. The suture bobbin 36 is disposed closer to the distal end of the first casing 12 than the plurality of needles 26 is to the distal end of the first casing. With this configuration, an end portion Lb of the suture L may be drawn by the suture hook 60 under an appropriate tension from the suture bobbin 36, thereby placing well-adjusted stitches N in edges of a cut T without too loose or too tight.

According to the suturing device 10 of the first illustrative embodiment, the first casing 12 has an elongated box shape and accommodates the needles 26. The second casing 14 has an elongated box shape and accommodates the suture hook 60. The second casing 14 has friction holes at a position where to hold to hold edges of a cut T. The friction holes 56*a* allow the needles 26, respectively, to pass therethrough. When the needles 26 holding the suture L at their tips respectively pass through the friction holes 56*a*, a friction force caused by contact between each of the friction holes 56*a* and the suture is greater than a friction force caused by contact between the circumferential wall 26*e* of each of the needles 26 and the suture L. Accordingly, when the needles 26 holding the suture L at their tips pass through the respective friction holes 56*a*, loops LP may be formed at the tips of the respective needles 26 readily. Other illustrative embodiments of the disclosure will be described below. A description will be provided mainly for the components or elements different from the first illustrative embodiment, and a description will be omitted for the common components or elements by assigning the same reference numerals thereto.

Second Illustrative Embodiment

Figure 29:
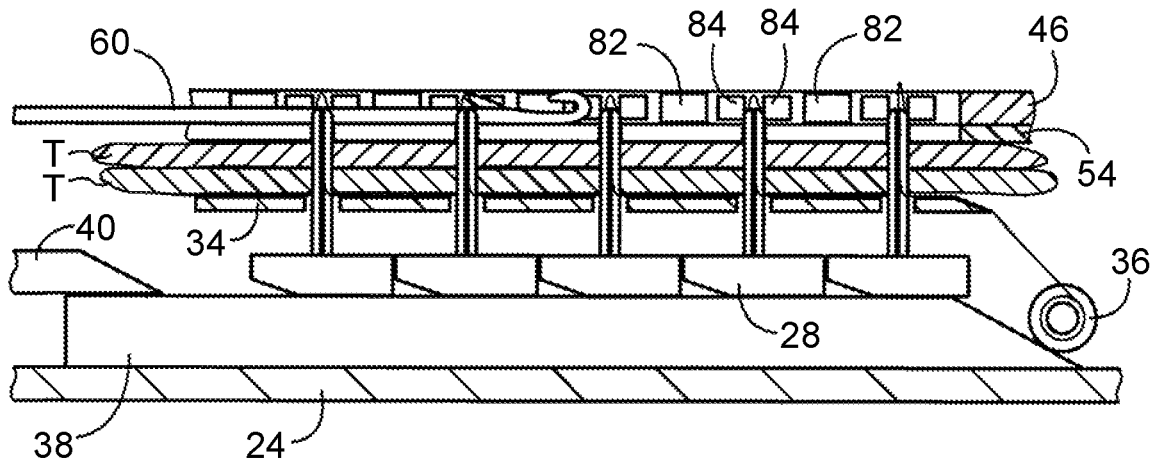
FIG. 29 illustrates a state corresponding to the state of FIG. 14 according a second illustrative embodiment of the disclosure, wherein a second casing includes suture hook guides and loop holding members.
Figure 30:
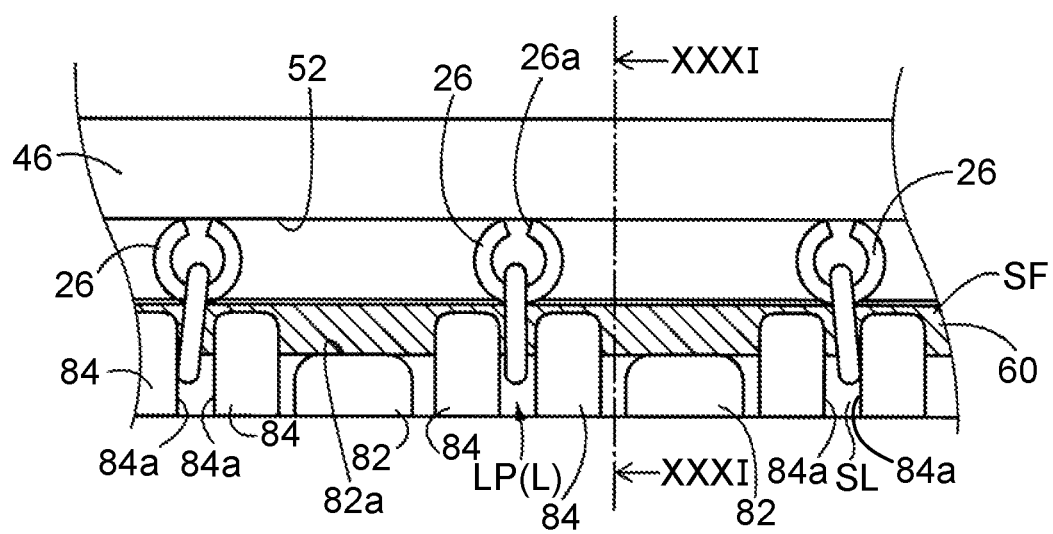
FIG. 30 is an enlarged view illustrating a state in which a suture hook guided by the suture hook guides passes through loops held by the loop holding members according the second illustrative embodiment of the disclosure.
Figure 31:
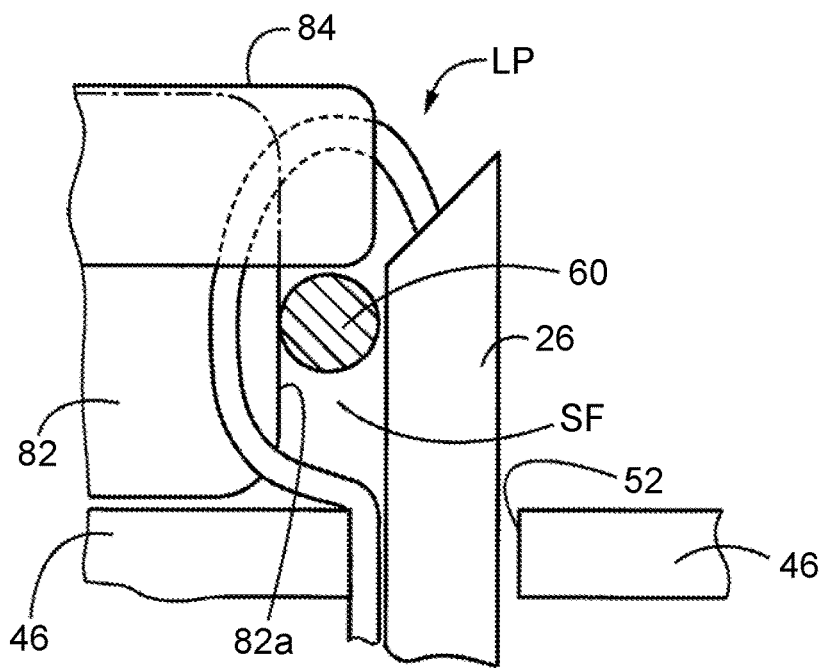
FIG. 31 is a cross-sectional view taken along line XXXI-XXXI of FIG. 30 according the second illustrative embodiment of the disclosure.

FIGS. 29, 30, and 31 illustrate one example of a second casing 14 according to a second illustrative embodiment. The second casing 14 includes suture hook guides 82 and loop holding members 84. The suture hook guides 82 are configured to guide movement of the suture hook 60 along the needle arrangement direction. The loop holding members 84 are configured to hold respective loops LP held by the tips of the needles 26 in such a manner that the loops LP are oriented extending perpendicular to a plane extending in the needle arrangement direction. In other embodiments, for example, either of the suture hook guides 82 and the loop holding members 84 may be omitted or the suture hook guides 82 and the loop holding members 84 may be integral with each other.

Each of the suture hook guides 82 has a restriction surface 82*a*. The set of restriction surfaces 82*a* and the plurality of needles 26 define a space SF therebetween. More specifically, for example, the space SF is provided between the set of the restriction surfaces 82*a* and a set of particular surfaces of the circumferential walls 26*e* of the needles 26. In the circumferential wall 26*e* of each needle 26, the particular surface is opposite to a surface having the slit 26*a*. The space SF is configured to receive the suture hook 60 and allow the suture hook 60 to move therein. Each of the loop holding members 84 has a pair of facing surfaces 84*a*. Each pair of facing surfaces 84*a* defines a space SL therebetween for receiving a loop LP formed at a tip of a corresponding needle 26. Each space SL is provided on a side of a corresponding needle 26 opposite to a side where the needle 26 has a slit 26*a* with respect to an axis of the needle 26. In another example, the second casing 14 may include a single suture hook guide 82 and a single loop holding member 84. In such a case, the suture hook guide 82 may have a plurality of restriction surfaces 82*a* and the loop holding member 84 may have a plurality pairs of facing surfaces 84*a*.

According to the second illustrative embodiment, the suture hook 60 is guided through the space SF defined between the set of the restriction surfaces 82*a* of the suture hook guide 82 and the set of the particular surfaces of the circumferential walls 26*e* of the needle 26. In the circumferential wall 26*e* of each needle 26, the particular surface is opposite to a surface having the slit 26*a*. Loops LP formed at the tips of the needles 26 such that the loops LP are oriented intersecting with the direction in which the suture hook 60 moves, that is, the needle arrangement direction. The loops LP oriented as such are held by the respective loop holding members 84. With this configuration, the suture hook 60 may reliably pass through the loops LP that is held by the tips of the needles 26 and formed on the side opposite to the side where the needle has the slit 26a. Consequently, the suturing device 10 may suture edges of a cut T reliably.

Figure 32:
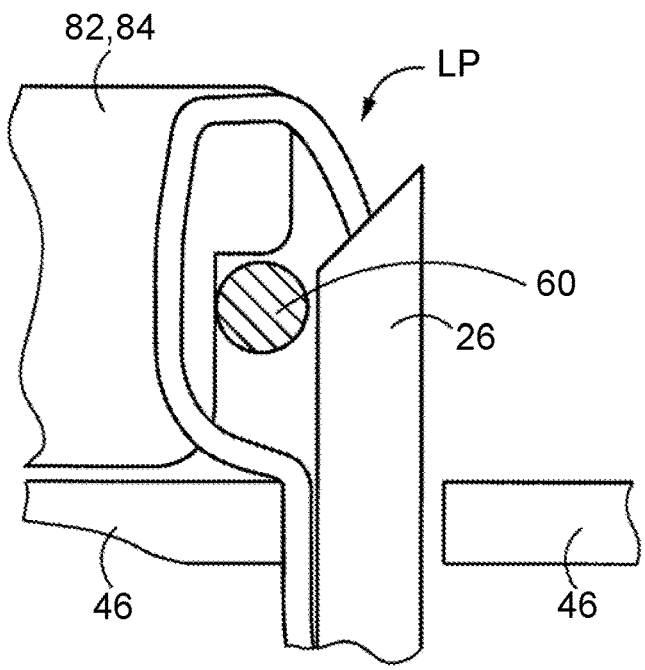
FIG. 32 illustrates a state corresponding to the state of FIG. 28 according the second illustrative embodiment of the disclosure, wherein a second casing includes a suture hook guide and a loop holding member that are integral with each other.

FIG. 32 illustrates another example of the second illustrative embodiment. The second casing 14 includes an injection molded combination of the suture hook guides 82 and the loop holding members 84. Such a configuration may thus reduce a parts count of the suturing device 10, thereby achieving a simplified configuration of the suturing device 10.

Third Illustrative Embodiment

Figure 33:
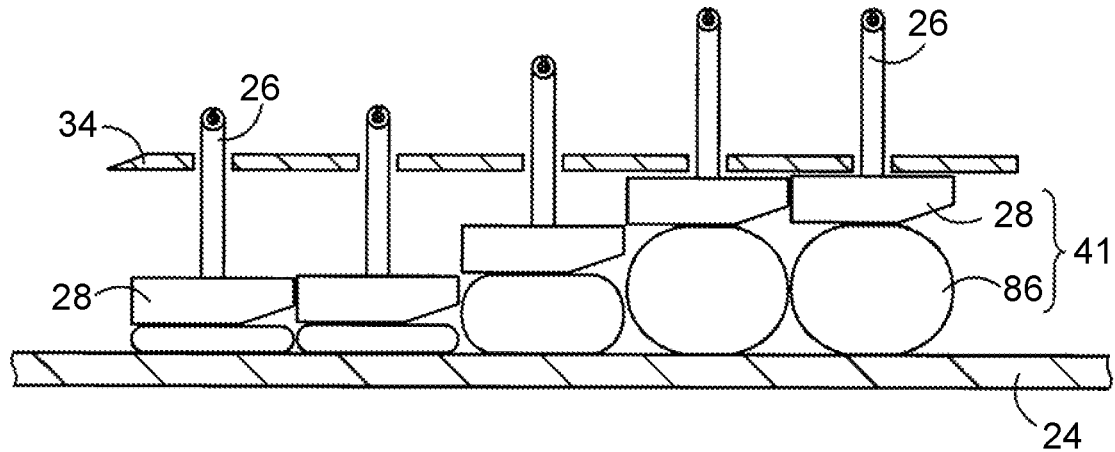
FIG. 33 illustrates a state corresponding to the state of FIG. 11 according to a third illustrative embodiment of the disclosure, a first casing includes balloons disposed under respective needle stands and one or more of the balloons push up corresponding needles.

Referring to FIG. 33, a third illustrative embodiment will be described. FIG. 33 illustrates another example of the needle moving mechanism 41. A first casing 12 includes a plurality of balloons 86 instead of the first needle pusher 38 and the second needle pusher 40. Each balloon 86 is expandable and disposed between a corresponding needle stand 28 and the bottom wall 24 of the first casing 12. The balloons 86 and the needle stands 28 may function as the needle moving mechanism 41. The balloons 86 are configured to expand by control of fluid pressure to be supplied into the respective balloons 86 to push up the respective corresponding needle stands 28 (e.g., move the respective corresponding needle stands 28 toward the second casing 14). In response to the needle stands 28 being pushed up by expansion of the respective balloons 86, the needles 26 penetrate edges of a cut T held by the first casing 12 and the second casing 14 and protrude from the pressure plate 34 by the second protrusion amount h2 or the first protrusion amount h1 selectively. In the third illustrative embodiment, each balloon 86 pushes up a respective corresponding needle stand 28. Nevertheless, in other embodiments, for example, a single balloon 86 may be configured to push up two or more of the needle stands 28.

Fourth Illustrative Embodiment

Figure 34:
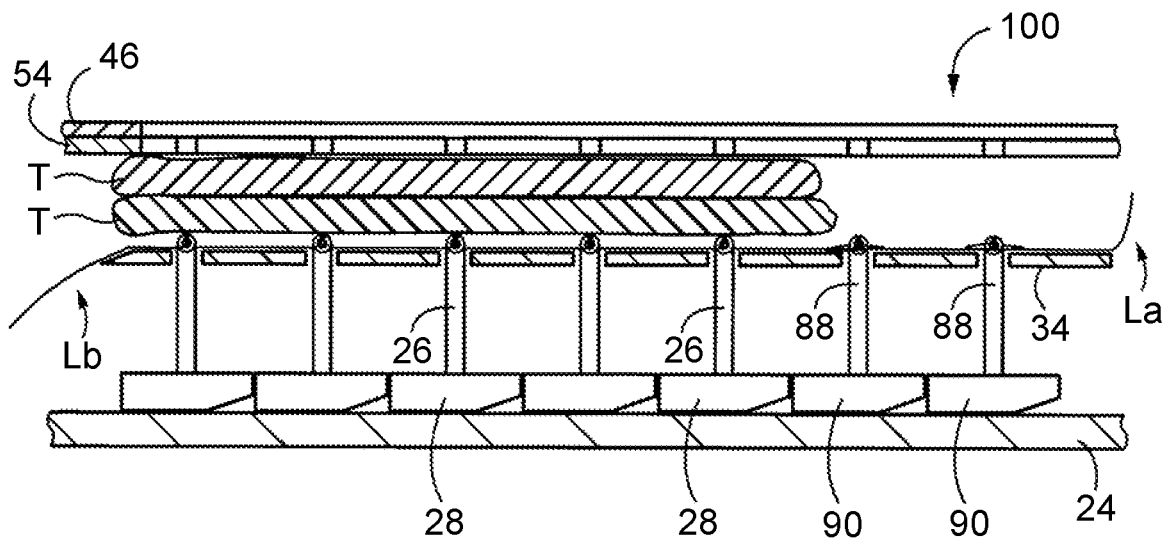
FIG. 34 illustrates a state corresponding to the state of FIG. 10 according a fourth illustrative embodiment of the disclosure, wherein a first casing includes knot forming needles.
Figure 35:
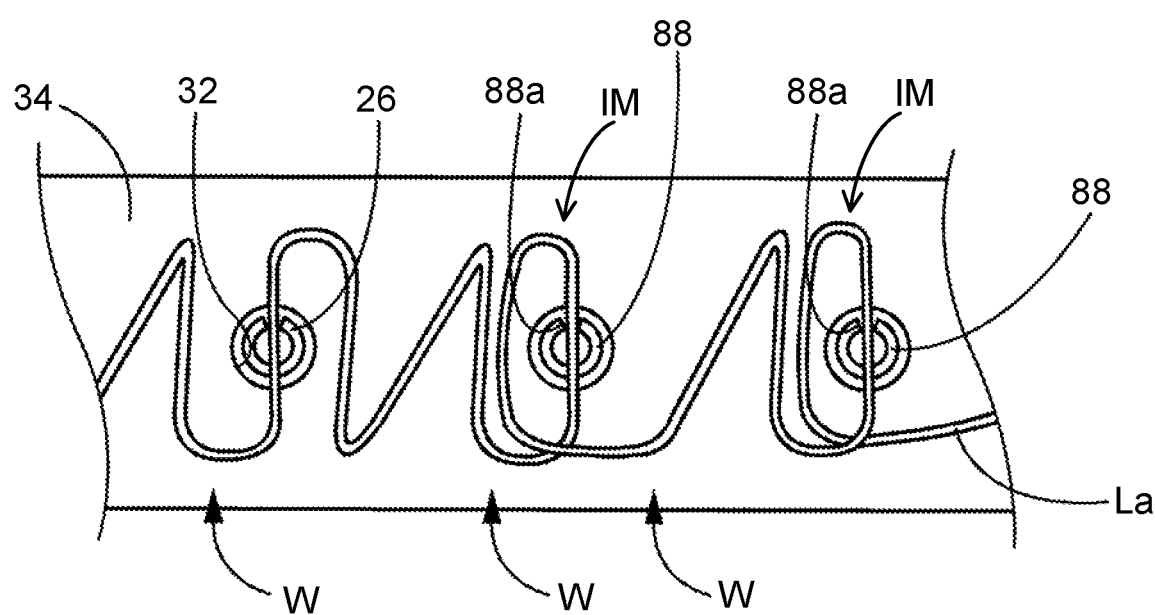
FIG. 35 is a top plan view of the first casing for explaining routing of a suture held by needles slightly protruding through the suture cover according to the fourth illustrative embodiment of the disclosure.

Referring to FIGS. 34 to 41, a description will be provided on a suturing device 100 according to a fourth illustrative embodiment. The suturing device 100 is configured to form a knot M using another procedure after stitches N are placed in edges of a cut T. The suturing device 100 includes a plurality of, for example, two knot forming needles 88 and a plurality of, for example, two needle stands 90 in addition to the needles 26 and the needle stands 28. The knot forming needles 88 and the needle stands 90 may function as a knot forming jig. Each knot forming needle 88 has the same configuration as the needles 26. Each needle stand 90 has the same configuration as the needle stands 28. The knot forming needles 88 and the needle stands 90 on which the knot forming needles 88 stand respectively are disposed next to each other in the needle arrangement direction. That is, the needles 26 and the knot forming needles 88 are aligned in the needle arrangement direction. In a state where the first casing 12 and the second casing 14 hold edges of a cut T therebetween, the knot forming needles 88 do not overlap the cut T, that is, are closer to the proximal end of the first casing 12 than a proximal-side end of the cut T is to the proximal end of the first casing 12. Each knot forming needle 88 has a slit 88a. The suture L is held by the tips of the needles 26 via the slits 26a and by the tips of the knot forming needles 88 via the slits 88a while the suture L has loosened portions W between the tips of the respective adjacent needles 26 and the tips of the knot forming needles 88. As illustrated in FIG. 35, the suture L is wound one time around each of the knot forming needles 88 to form an incomplete knot IM.

Hereinafter, a description will be provided on a procedure for forming stitches and a knot.

FIG. 34 illustrates the suturing device 100 that is opened to increase a distance between the first casing 12 and the second casing 14 and is placed at an appropriate position so that the first casing 12 and the second casing 14 are located on opposite sides of edges of a cut T. FIG. 34 corresponds to the preliminary preparation step of FIG. 10.

Figure 36:
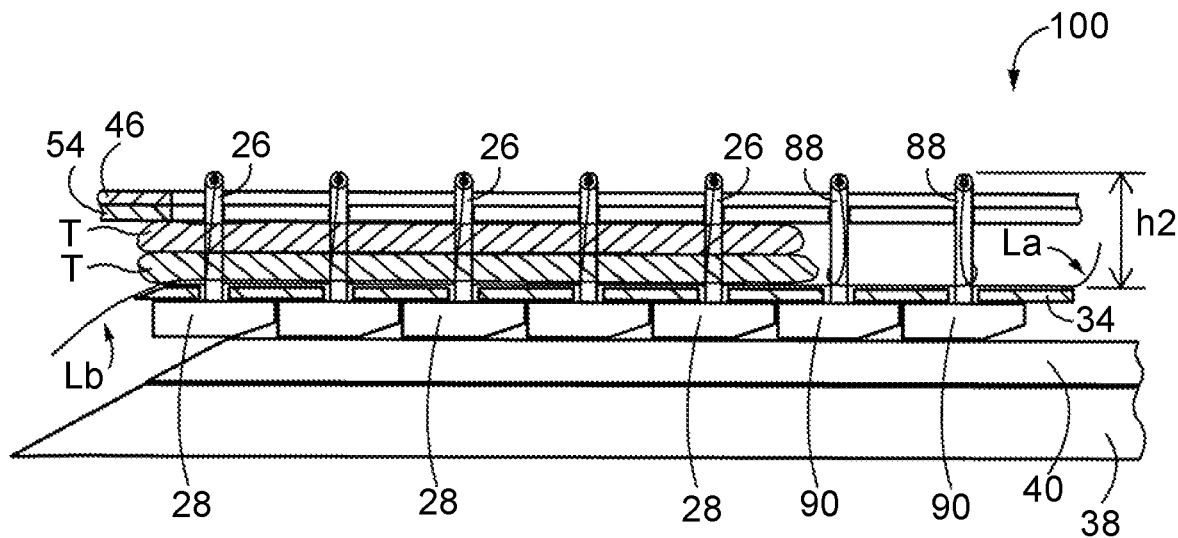
FIG. 36 illustrates a state after the state of FIG. 35, illustrating the state in which a first needle pusher and a second needle pusher push up all of the needles by their forward movement according the fourth illustrative embodiment of the disclosure.

FIG. 36 illustrates the suturing device 100 that has been closed to decrease the distance between the first casing 12 and the second casing 14, thereby sandwiching the edges of the cut T between the first casing 12 and the second casing 14.

In addition, the needles 26 and the knot forming needles 88 protrude from the pressing plate 34 by the second protrusion amount h2 by forward movement of the first needle pusher 38 and the second needle pusher 40 toward the distal end of the first casing 12. In such a state, the needles 26 penetrate the edges of the cut T and pass through the friction holes 56a of the friction plate 54 disposed on the bottom wall 46 of the second casing 14 and the slot 52 of the bottom wall 46 of the second casing 14. FIG. 36 corresponds to the needle penetration step of FIG. 12.

Figure 37:
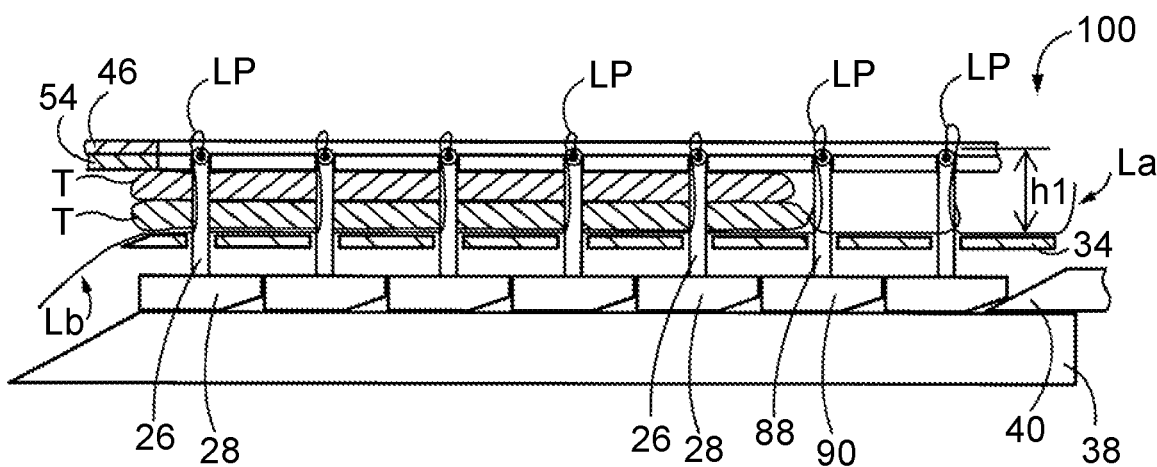
FIG. 37 illustrates a state in which a loop is formed at a tip of each of the needles by downward movement of the needles from the position of FIG. 36 according the fourth illustrative embodiment of the disclosure.

FIG. 37 illustrates the suturing device 100 in which the second needle pusher 40 has been moved backward toward the proximal end of the second casing 14. As the second needle pusher 40 is moved backward toward the proximal end of the second casing 14, as illustrated in FIG. 37, the needle stands 28 and 90 are moved downward one after another to be located at the first height where the needle stands 28 and 90 are on the first positioning surface 38b of the first needle pusher 38. Thus, the needles 26 and the knot forming needles 88 are partially retracted below the pressing plate 34. Consequently, the needles 26 and the knot forming needles 88 are lowered to protrude from the pressing plate 34 by the first protrusion amount h1. In such a needle lowering step, a loop LP is formed at the tip of each of the needles 26 by friction caused between the suture L held by the tip of the needle 26 via the slit 26a and the friction plate 54, and is also formed at the tip of each of the knot forming needles 88 between the suture L held by the tip of the knot forming needle 88 via the slit 88a and the friction plate 54. FIG. 37 corresponds to the loop forming step of FIG. 13.

Figure 38:
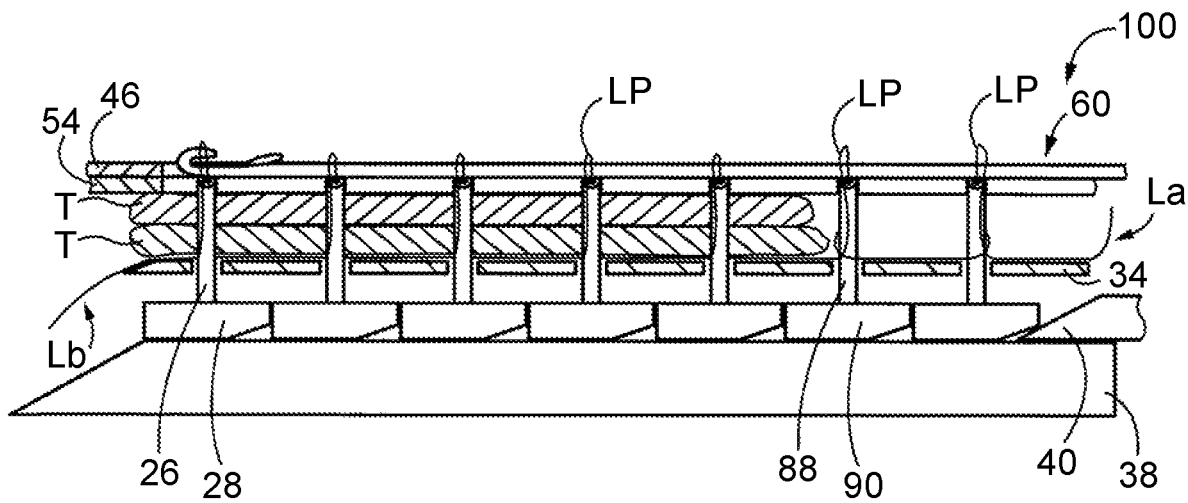
FIG. 38 illustrates a state after the state of FIG. 37, illustrating the state in which a suture hook is inserted into the loops formed at the tips of the needles by forward movement of the suture hook according the first illustrative embodiment of the disclosure.

As illustrated in FIG. 38, as the suture hook 60 is moved forward toward the distal end of the second casing 14, the hook 62 disposed at the distal end of the suture hook 60 passes through a loop LP formed at the tip of each of the needles 26 and knot forming needles 88. FIG. 38 illustrates a state after the forward movement of the suture hook 60 is completed. FIG. 38 corresponds to the suture hook insertion step of FIG. 15.

Figure 39:
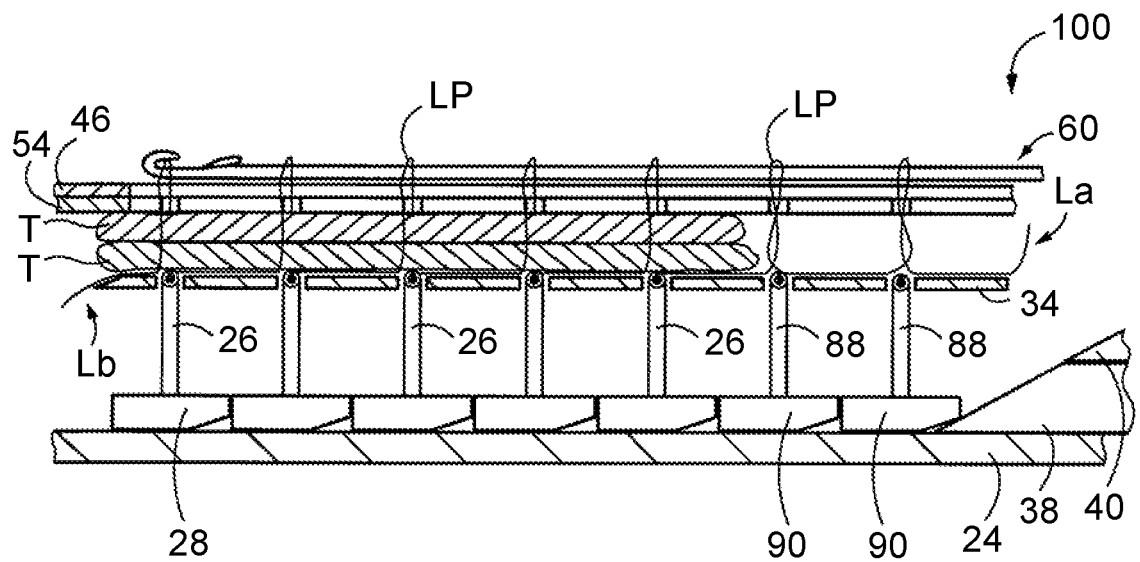
FIG. 39 illustrates a state after the state of FIG. 38, illustrating the state in which the suture hook has reached a furthest position by its further forward movement from the position of FIG. 38 according the fourth illustrative embodiment of the disclosure.

As illustrated in FIG. 39, as the first needle pusher 38 is moved backward toward the proximal end of the second casing 14, the needle stands 28 and 90 are moved downward one after another and thus located on the bottom wall 24 of the first casing 12. That is, in response to the needle stands 28 and 90 being lowered to such a position, the needles 26 and the knot forming needles 88 are further retracted below the pressing plate 34 so that the needles 26 are removed from the edges of the cut T. FIG. 39 corresponds to the needle removal step of FIG. 16.

Figure 40:
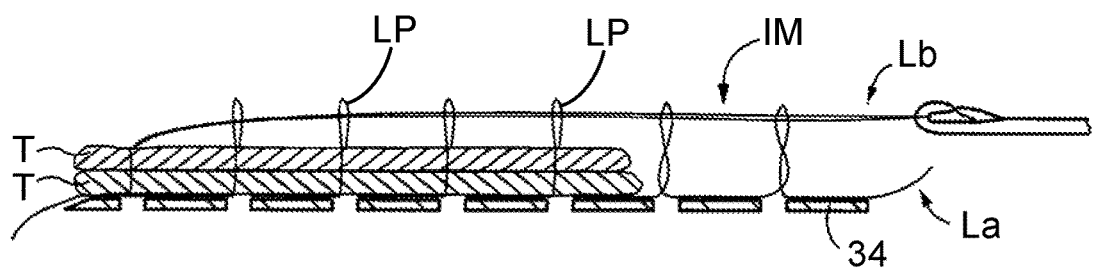
FIG. 40 illustrates a state after the state of FIG. 39, illustrating the state in which the suture hook is pulled out from loops by its backward movement according the fourth illustrative embodiment of the disclosure.
Figure 41:
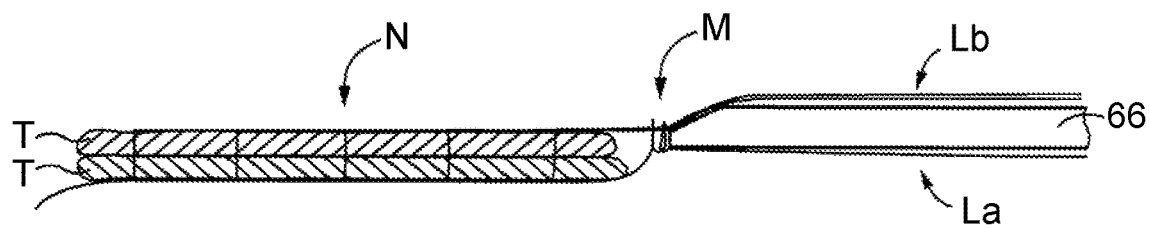
FIG. 41 illustrates a state in which a knot formed from incomplete knots is firmly tightened by a knot forming jig that is moved forward while a suture is tightened according the fourth illustrative embodiment of the disclosure.

Then, a knot M is formed as described below on the end portions La and Lb of the suture L used for placing stitches N to suture the edges of the cut T. Referring to FIGS. 40 and 41, a description will be provided on a procedure to form the knot M. FIG. 40 illustrates the edges of the cut T and the suture L after the needles 26 and the knot forming needles 88 are retracted below the pressing plate 34. Stitches N are formed by the end portion Lb of the suture L and loops Lp. More specifically, for example, the end portion Lb of the suture L extending from the suture bobbin 36 is drawn by the suture hook 60 to pass through each loop LP formed penetrating the edges of the cut T. In addition, incomplete knots IM are formed by the end portion Lb of the suture L and loops Lp. More specifically, for example, the end portion Lb of the suture L is drawn by the suture hook 60 to pass through each loop LP formed at the tip of a corresponding knot forming needle 88. FIG. 40 corresponds to FIG. 21.

After that, in the state of FIG. 40, the knot forming jig 66 functioning as the knot pusher is moved forward toward the distal end of the second casing 14. Thus, the end portions La and Lb of the suture L are both tightened, thereby forming a knot M as illustrated in FIG. 41. For example, the knot M is a square knot illustrated in FIG. 26.

According to the suturing device 100 of the fourth illustrative embodiment, the same effects may be achieved as that achieved by the suturing device 10 according to the other illustrative embodiments. The suturing device 100 according to the fourth illustrative embodiment includes the knot forming needles 88. The suture L is wound around each of the knot forming needles 88 for forming a certain knot M and then loops LP are formed at the tips of the knot forming needles 88. Thereafter, the suture hook 60 catching and holding the suture L passes through each loop Lp to form the certain knot M in the suture L held by the suture hook 60. With this configuration, a knot M may be formed by tying an end portion Lb of the suture L and an end portion La of the suture L, thereby stably fastening stitches N placed in edges of a cut T. The end portion Lb may pass through loops LP formed at the tips of the respective needles 26 together with the suture hook 60. The end portion La may extend from a portion of the suture L that forms the loops LP and is wound around the knot forming needles 88.

While the disclosure has been described in detail with reference to the specific embodiments thereof, these are merely examples, and various changes, arrangements and modifications may be applied therein without departing from the spirit and scope of the disclosure.

The suture L may be made of any material suitable for ligation. The suture L may be, for example, a natural suture, a synthetic suture, a metallic suture, or a composite suture. The natural suture may be a monofilament or multifilament suture made from plant or animal fibers. The synthetic suture may be a monofilament or multifilament suture made of synthetic fibers. The metallic suture may be a monofilament or multifilament suture made of metallic wires. The composite suture may be made of natural fibers and synthetic fibers.

In the illustrative embodiments, the tubular member 16 has circular shape in cross section. Nevertheless, in other embodiments, for example, a tubular member may have a polygonal shape or an oval shape in cross section instead.

In the illustrative embodiments, the first casing 12 and the second casing 14 both have a rectangular shape in cross section. Nevertheless, in other embodiments, for example, the first casing 12 and the second casing 14 may be tubular members each having a circular shape, an oval shape, or a polygonal shape in cross section.

The cylindrical drive shaft and the operating rods disposed in the tubular member 16 may be configured to, in one example, be operated manually, or in another example, be operated by an actuator controlled based on a prestored program.

In the illustrative embodiments, a knot M is formed after stitches N are placed in edges of a cut T. Nevertheless, in other embodiments, for example, a knot M might not necessarily be formed after stitches N are placed in edges of a cut T.

In the illustrative embodiments, the needles 26 are provided in a one-to-one correspondence to the needle stands 28. Nevertheless, in other embodiments, for example, a plurality of, for example, two each of the needles 26 may be provided for each of the needle stands 28.

In the suturing device 100, as the knot forming jig, the knot forming needles 88 having the same shape as the needles 26 are used. Nevertheless, in other embodiments, for example, each knot forming needle 88 might not necessarily have a sharp point at its tip, that is, may be a rod-shaped needle-like member having a shallow slit 88a or a thready needle-like member.

What is claimed is:

1. A suturing device comprising:
   first and second holding members configured to move toward and away from each other to sandwich therebetween edges of a cut;
   a plurality of needles disposed at the first holding member and aligned in a needle arrangement direction with their points pointing to the second holding member, the plurality of needles configured to hold a suture at tips thereof and penetrate the edges of the cut;
   a needle moving mechanism configured to move the plurality of needles toward the second holding member, thereby allowing the plurality of needles holding the suture at the respective tips to penetrate the edges of the cut;
   a suture hook disposed at the second holding member and configured to move along the needle arrangement direction to catch the suture that has reached the second holding member via the edges of the cut by movement of the plurality of needles toward the second holding member by the needle moving mechanism; and
   a knot forming jig disposed at a proximal end portion of the second holding member, wherein the suture hook is disposed at the proximal end portion of the second holding member in such a manner to move along the needle arrangement direction,
   wherein the suture is wound around the knot forming jig to form a loop in the suture for forming a certain knot, and
   wherein the suture hook holding the suture is configured to pass through, between the loop of the wound suture and the knot forming jig to allow the knot forming jig to form the certain knot in the suture held by the suture hook.

2. The suturing device according to claim 1, wherein the plurality of needles are arranged at equal intervals.

3. The suturing device according to claim 1, wherein each of the plurality of needles has a slit defined in a tip portion thereof,
   wherein the slit is configured to allow a corresponding needle of the plurality of needles to releasably hold the suture at the tip portion of the needle, and wherein the slit extends in the tip portion of each of the plurality of needles in a direction intersecting with a direction in which the suture hook moves.

4. The suturing device according to claim 3,
wherein the second holding member includes a plurality of loop holding members configured to respectively hold loops held by the tips of the plurality of needles in such a manner that the loops are oriented intersecting with a plane extending in the needle arrangement direction, wherein the loops have been formed at the tips of the plurality of needles by movement of the plurality of needles away from the second holding member by the needle moving mechanism, and
wherein each of the loop holding members has a pair of facing surfaces defining therebetween a space for receiving a corresponding loop of the loops held by the tips of the plurality of needles, and
wherein each of the spaces is provided on a side of a corresponding needle of the plurality of needles opposite to a side where the needle has the slit with respect to an axis of the needle.

5. The suturing device according to claim 3,
wherein each of the plurality of needles has an acute angled tip and a circumferential wall,
wherein, in each of the plurality of needles, the slit extends in at least a particular portion of the circumferential wall along an axial direction of the needle from a point of the acute angled tip to a proximal end of the needle opposite to the acute angled tip in the axial direction of the needle, and
wherein the particular portion of the circumferential wall extends from the point of the acute angled tip of the needle.

6. The suturing device according to claim 5,
wherein the second holding member includes a suture hook guide configured to guide movement of the suture hook along the needle arrangement direction,
wherein the suture hook guide has a plurality of restriction surfaces, and the plurality of restriction surfaces and the plurality of needles define a space therebetween,
wherein the space is provided between the plurality of restriction surfaces and particular surfaces of the circumferential walls of the plurality of needles, and
wherein in the circumferential wall of each of the plurality of needles, the particular surface is opposite to a surface having the slit.

7. The suturing device according to claim 5,
wherein the second holding member includes:
a plurality of suture hook guides configured to guide movement of the suture hook along the needle arrangement direction; and
a plurality of loop holding members configured to respectively hold loops held by the tips of the plurality of needles in such a manner that the loops are oriented intersecting with a plane extending in the needle arrangement direction, wherein the loops have been formed at the tips of the plurality of needles by movement of the plurality of needles away from the second holding member by the needle moving mechanism,
wherein each of the plurality of suture hook guides has a restriction surface,
wherein the plurality of restriction surfaces and the plurality of needles define a first space therebetween,
wherein the first space is provided between the plurality of restriction surfaces and particular surfaces of the circumferential walls of the plurality of needles,
wherein in the circumferential wall of each of the plurality of needles, the particular surface is opposite to a surface having the slit,
wherein each of the loop holding members has a pair of facing surfaces defining therebetween a second space for receiving a corresponding loop of the loops held by the tips of the plurality of needles,
wherein each of the second spaces is provided on a side of a corresponding needle of the plurality of needles opposite to a side where the needle has the slit with respect to an axis of the needle, and
wherein the plurality of suture hook guides and the plurality of loop holding members are integral with each other.

8. The suturing device according to claim 1, further comprising at least one needle stand supporting proximal ends of the plurality of needles with the points of the plurality of needles pointing to the second holding member, and
wherein the needle moving mechanism is further configured to move the at least one needle stand toward the second holding member.

9. The suturing device according to claim 8,
wherein the at least one needle stand includes a plurality of needle stands each supporting a proximal end of a corresponding needle of the plurality of needles.

10. The suturing device according to claim 9,
wherein the first holding member includes a needle stand guide configured to guide movement of the plurality of needle stands in such a manner to restrict the plurality of needle stands from moving in the needle arrangement direction and allow the plurality of needle stands to move toward the second holding member.

11. The suturing device according to claim 9,
wherein the needle moving mechanism includes a pusher configured to move along the needle arrangement direction and move the plurality of needles toward the second holding member to protrude from the first holding member by engaging the plurality of needle stands.

12. The suturing device according to claim 9,
wherein the needle moving mechanism includes:
a first pusher disposed at the first holding member and configured to move along the needle arrangement direction, the first pusher having a first inclined surface and a first positioning surface, the first inclined surface being configured to, by engaging the plurality of needle stands one after another, move the plurality of needles toward the second holding member to protrude from the first holding member, the first positioning surface being a flat surface contiguous from the first inclined surface and being configured to position the plurality of needle stands at a first height; and
a second pusher disposed at the first holding member and configured to move along the needle arrangement direction, the second pusher having a second inclined surface and a second positioning surface, the second inclined surface being configured to, by engaging, one after another, the plurality of needle stands that have been moved toward the second holding member by the first pusher, move the plurality of needles toward the second holding member to further protrude from the first holding member, the second positioning surface being a flat surface contiguous from the second inclined surface and being configured to position the plurality of needle stands at a second height.

13. The suturing device according to claim 9,
wherein the needle moving mechanism further includes a plurality of balloons,
wherein each of the plurality of balloons is disposed between a corresponding needle stand of the plurality of needle stands and the first holding member, and
wherein the balloons are configured to expand by fluid injection to move the plurality of needle stands toward the second holding member.

14. The suturing device according to claim 9,
wherein the needle moving mechanism further includes return springs configured to urge the plurality of needle stands toward the first holding member.

15. The suturing device according to claim 1,
wherein the knot forming jig has an elongated shape and is configured to move along the needle arrangement direction.

16. The suturing device according to claim 1, wherein the knot forming jig includes a needle-like member.

17. The suturing device according to claim 1,
wherein the knot forming jig functions as a tightening jig configured to push and secure the certain knot from a proximal-end side of the second holding member with respect to the formed knot.

18. The suturing device according to claim 1,
wherein the first holding member includes a bobbin holding the suture,
wherein the bobbin is disposed closer to a distal end of the first holding member than the plurality of needles is to the distal end of the first holding member.

19. The suturing device according to claim 1,
wherein the first holding member includes an elongated box-shaped casing accommodating the plurality of needles,
wherein the second holding member includes an elongated-box-shaped casing accommodating the suture hook,
wherein the second holding member has a plurality of friction holes at a position where to hold the edges of the cut,
wherein the plurality of friction holes allow the plurality of needles, respectively, to pass therethrough, and
wherein when the plurality of needles holding the suture at the tips thereof respectively pass through the plurality of friction holes, a friction force caused by contact between each of the plurality of friction holes and the suture is greater than a friction force caused by contact between a circumferential wall of each of the plurality of needles and the suture.

* * * * *